(12) United States Patent
Seabrook, Jr. et al.

(10) Patent No.: US 7,972,635 B2
(45) Date of Patent: Jul. 5, 2011

(54) POLYMER COATINGS CONTAINING PHYTOCHEMICAL AGENTS AND METHODS FOR MAKING AND USING SAME

(76) Inventors: Samuel G. Seabrook, Jr., Mr. Pleasant, SC (US); Glenn Stockum, Arlington, TX (US)

( * ) Notice: Subject to any disclaimer, the term of this patent is extended or adjusted under 35 U.S.C. 154(b) by 505 days.

(21) Appl. No.: 11/971,107

(22) Filed: Jan. 8, 2008

(65) Prior Publication Data

US 2008/0175812 A1 Jul. 24, 2008

Related U.S. Application Data

(63) Continuation-in-part of application No. PCT/US2006/026753, filed on Jul. 10, 2006.

(60) Provisional application No. 60/954,395, filed on Aug. 7, 2007, provisional application No. 60/697,818, filed on Jul. 8, 2005.

(51) Int. Cl.
*A61K 36/752* (2006.01)
*A61K 36/81* (2006.01)
*A61K 36/00* (2006.01)

(52) U.S. Cl. ......... 424/736; 424/725; 424/760; 424/776

(58) Field of Classification Search .................. None
See application file for complete search history.

(56) References Cited

U.S. PATENT DOCUMENTS

| 5,397,385 | A | 3/1995 | Watts |
| 5,492,696 | A * | 2/1996 | Price et al. .............. 424/417 |
| 5,906,825 | A | 5/1999 | Seabrook, Jr. et al. |
| 6,060,046 | A | 5/2000 | Steinberg et al. |
| 6,635,692 | B1 | 10/2003 | Christie et al. |
| 6,692,557 | B1 | 2/2004 | De Nys et al. |
| 7,582,783 | B2 * | 9/2009 | Blum ..................... 554/52 |
| 2005/0080160 | A1 | 4/2005 | Seabrook, Jr. |

FOREIGN PATENT DOCUMENTS

| WO | WO 99/20258 | 4/1999 |
| WO | WO 2005/017051 | * 2/2005 |

* cited by examiner

*Primary Examiner* — Christopher R. Tate

(57) ABSTRACT

This invention relates to compositions comprising a polymer base incorporating antifouling compositions suitable for use in aquaculture, marine and architectural systems as paints, structures or coatings. In particular, the present invention relates to a polymer based coating incorporating a biocidal antifouling composition suitable for use with aquaculture equipment. The present invention provides polyethylene compositions and latex compounds which may comprise at least one environmentally benign phytochemicals suitable for use in preventing the colonization of a treated surface by a variety of biological species. The compositions of the invention may further comprise control release agents such as, for example, micro-encapsulation of the phytochemicals to maintain sustained and prolonged release of the biocidal agents at the treated surface.

2 Claims, 3 Drawing Sheets

POLYMER COATINGS CONTAINING PHYTOCHEMICAL AGENTS AND METHODS FOR MAKING AND USING SAME

INCORPORATION BY REFERENCE

This application is a continuation-in-part application of international patent application Serial No. PCT/US06/26753 filed Jul. 10, 2006, claims priority to U.S. Provisional Patent Application No. 60/697,818 filed Jul. 8, 2005. This application also claims priority to U.S. Provisional Patent Application No. 60/954,395 entitled "ANTIFOULING COATINGS, PAINTS AND POLYMERS CONTAINING PHYTOCHEMICAL BIOCIDAL AGENTS" filed Aug. 7, 2007. Reference is also made to U.S. Provisional Patent Application No. 60/796,661 entitled "PAINTS, COATINGS, AND POLYMERS CONTAINING MICROENCAPSULATED BIOCIDAL PHYTOCHEMICAL AGENTS" filed May 2, 2006.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

This invention relates generally to compositions which may comprise a polymer base incorporating antifouling compositions suitable for use in aquaculture, marine and architectural systems as paints, structures or coatings. In particular, the present invention relates to a polymer based coating incorporating a biocidal antifouling composition suitable for use with aquaculture equipment. This invention also relates to polymer coatings; UHMW polyethylene, VHMW polyethylene, latex compounds and latex compounds incorporating biocidal phytochemical agents. The invention also relates to compositions which may comprise microencapsulated biocidal phytochemicals suitable for use as architectural, marine, aquaculture systems paints, structures and coatings which may be suitable for use as protective wood treatments, filter membranes, catheter coatings and food wraps and containers.

BACKGROUND OF THE INVENTION

Undesirable growth of animal and plant life on submerged surfaces results in major costs to the shipping industry, aquaculture and any other industries that relies on equipment submerged in a marine or freshwater environment. This marine growth, known as fouling, can seriously diminish the performance of a ship's hull through the water, as well as causing structural damage. Both marine and freshwater vessels are susceptible to bottom fouling that can result in significant economic penalties.

Aquaculture is the business of the regulation and cultivation of water plants and animals for human use or consumption. Typically, there is a rapid build up of marine fouling on the structures used in aquaculture such as, ropes, nets, buoys, cages and traps, which is costing the industry billions of dollars annually through labor intense maintenance to clean these materials. Aquaculture is an industry that produces at least 50 billion dollars per year globally and there is not a known environmentally safe antifouling coating for aquaculture systems. As a result the industry loses approximately 3 to 5 billion dollars per year in lost production due to the results of fouling. Another 1 billion dollars per year is spent on the manual cleaning of these systems.

Historically, toxic chemicals including heavy metals and their salts have been added to marine paints to control the build up of organisms on vessel hull bottoms and structures. Two chemicals, tributyltin (TBT) and cuprous oxide (copper) have been in commercial use for decades as antifouling agents in marine paints. However, tributylin is now banned worldwide due to its high toxicity to free-floating marine organisms when leached into the surrounding water. Cuprous oxide is also of concern because of the build-up of high concentrations of copper ions in harbor sediment, again after leaching from the anti-fouling coatings.

Both chemicals, therefore, have a detrimental impact on the marine environment worldwide and replacements are eagerly sought. However, attempts to replace the current toxic chemicals with alternatives that are non-toxic when released into the surrounding water, or mechanical alternatives that could dislodge attaching marine growths, have met with limited success. Furthermore, neither tributyltin (TBT) nor cuprous oxide can be used in the aquaculture industry that requires agents that will not adversely affect the growth of the farmed fish themselves and which do not provide danger to the ultimate consumer. Antifouling coatings, including such as marine paints, typically comprise combinations of binders, pigments, additives and solvents. The binders determine the characteristics of the antifouling, including leaching of biocidal components into the surrounding water. Pigments include the antifouling toxic agent(s) and various fillers. The solvents provide the application properties, while the additives are stabilizers for extended shelf life and to prolong the efficacy of the paint or coating once applied to the ship surface.

The three classes of antifouling paints currently in use are leaching (hard and soft), ablative coatings and self-polishing coatings (polymers). Leaching (hard and soft) is the process whereby the toxicant comes out of the paint at a controlled and sustained rate. Ablative coatings comprise a soluble matrix in the coating (film) that is made up of the natural product rosin and hydrocarbons that act as a binder in the soluble matrix. Self-polishing antifoulings are of two types, those containing tin (TBT) and those that are tin-free.

Non-toxic and self-polishing polymer coatings such as silicones, TEFLON™ and epoxies are coatings that have offered possible alternatives to marine paints containing toxic antifouling agents, but have found little or no use in the aquaculture industry. Because of the slick surface marine microorganisms have a difficult time attaching. However, these non-toxic coatings would be further enhanced with the addition of environmentally benign phytochemical-based antifouling compositions.

Non-marine structural surfaces may be also subject to undesirable biocontamination. For example, in buildings where high humidity and temperature are encountered, mildew, fungi or bacterial growth are encouraged that can release airborne allergens and cause asthma and other ailments. Medical facility surfaces demand substantially reduced level of contaminating level of microbial colonization, usually achieved by disinfection, to avoid nosocomial infections. If persons or animals are to come into direct contact with architectural or other surfaces, it is desirable that active biocidal compounds that may be incorporated in the protective coatings be both long lasting and present minimal environmental hazards.

There is still an existing need, however, for effective and economical antifouling coatings that may allow the aquaculture industry to reduce the labor intense problem of cleaning fouling from aqua culture equipment or which do not present an environmental danger when applied to ship hulls. Phytochemicals are known which have broad activity, preventing or inhibiting the growth of a broad spectrum of microbes, as well as exhibiting efficacy against a range of potentially marine fouling organisms such as barnacles and algae. For example, biocidal phytochemicals have been incorporated into polymeric films useful for wrapping and protecting foodstuffs during storage as (see, e.g., U.S. Pat. No. 5,906,825). *Capsicum*, at high pungency levels, has been added to marine paints to prevent the fouling of ships bottoms (see, e.g., U.S. Pat. No. 5,397,385). Furanones from marine algal sources have been incorporated into coatings of aquaculture equipment (see, e.g., U.S. Pat. Nos. 6,692,557, 6,635,692 and 6,060,046).

Phytochemicals that leach out of paint dilute and disperse extremely well into water and their biodegradability ensures they do not accumulate to unacceptable levels in the environment. Their antifouling effect particularly resides in a surface effect that takes place only in the immediate environment of the painted or coated surface. This characteristic makes the compositions of the present invention comprising phytochemicals compatible with UHMW polyethylene and VHMW polyethylene, silicones and latex compounds.

A need still exists, however, for a safe, environmentally friendly alternative to toxic additives in marine paints and architectural coatings, which does not comprise a highly pungent level of *capsicum* that may be harmful to the applicant of the paint and to individuals who may come into direct contact with a treated surface.

Citation or identification of any document in this application is not an admission that such document is available as prior art to the present invention.

SUMMARY OF THE INVENTION

The present invention provides polymer-based compositions, including, but not limited to, latex-based compositions, paints, coatings and structural materials that incorporate at least one environmentally benign antifouling composition for use in preventing or inhibiting the colonization of a treated surface by a variety of biological species. Phytochemicals that leach out of paint dilute and disperse extremely well into water and their biodegradability ensures they do not accumulate to unacceptable levels in the environment. Their antifouling effect particularly resides in a surface effect that takes place only in the immediate environment of the painted or coated surface. This characteristic makes the compositions of the present invention comprising phytochemicals compatible with leaching coatings, ablative coatings and self-polishing coatings (polymers).

One aspect, therefore, of the invention relates to an antifouling base composition comprising *capsicum*, menthol and tea tree oil which may be incorporated into coatings or other polymer based compositions. The antifouling activity of the base composition of the invention may be further enhanced by the addition of at least one other antifouling agent or combination of agents. In particular, pomegranate extract and grapefruit seed extract may be advantageously added. It is also contemplated that at least one protease may be included in the antifouling composition. The combination of antifouling agents of the present invention is believed to inhibit or destroy biofilms which rapidly form on a surface immersed in marine or fresh water. This multi-step process begins by the non-specific attachment of proteinaceous and other soluble organic material freely floating in the water. The attached protein provides a substrate that can then be colonized by microorganisms and subsequently by the foulant life forms.

The invention may further encompass antifouling compositions which may be diluted with water. Although it is contemplated that the antifouling compositions of the invention are diluted with water before admixing with a polymer base, it is also contemplated that the antifouling compositions may be added directly to a body of water to reduce or destroy fouling therein.

The present invention provides paint and coating compositions which may comprise at least one environmentally benign antifouling agent suitable for use in preventing the colonization of a treated surface by a variety of biological species. One aspect, therefore, of the invention is antifouling marine coatings suitable for application to aquaculture apparatus to provide extended protection from biofouling. The present invention therefore provides polymeric coatings comprising a polymer and at least one biocidal phytochemical and which may be applied to structures such as ropes and cages used in aquaculture and which are susceptible to marine organism overgrowth. The polymer materials of the invention incorporating the antifouling agents may also be used as structural material of such aquaculture equipment. The present invention further provides antifouling polymer-based materials such as polyethylene or latex polymers. The present invention also provides coating compositions such as, but not limited to, paint coatings, incorporating environmentally benign antifouling compositions of the invention, suitable for application to wood and wood products.

The present invention further encompasses polymer films incorporating antifouling compositions that may be used to coat any substrate to prevent or inhibit the growth of organisms thereon. For example, glass fiber may be pre-treated with a latex or other polymer coating that incorporates the antifouling agents menthol, tea tree oil, *capsicum*, grape fruit seed extract and/or pomegranate extract, or isolated components thereof, or any combination having biocidal activity. Advantageously, the polymer will comprise the antifouling compositions of the invention. Such treated glass-fiber may then be used to form filters, used in insulation, etc wherein there is the possibility of undesirable biogrowth forming on the fibers. The biocidal coatings thereof according to the present invention will be able to prevent the growth of microorganisms, fungi and the like that may colonize the filter material during storage or use.

The selection of the appropriate coating material will depend on the application for the use of biocidal antifouling agents. For example, the coating material should be resistant to the admixed agent(s) and not, for example, readily dissolved by them.

The present invention provides polyethylene compositions, latex compounds and latex compounds that may comprise at least one environmentally benign phytochemicals suitable for use in preventing the colonization of a treated surface by a variety of biological species. One aspect, therefore, of the invention is antifouling marine coatings for materials used in the aqua culture industry using UHMV & VHMV polyethylene and other types of compression molding and latex compounds. UHMV (Ultra High Molecular Weight) polyethylene polymer is a linear polyethylene with a molecular weight in the range of 3,000,000 to 10,000,000. This value represents the "average molecular weight". Therefore, UHMW polymers have a molecular weight average 10 times that of conventional high density polyethylene resins. The higher molecular weight is what gives UHMW polymers a unique combination of characteristics making it more suitable for many applications where lower molecular weight grades fail. VHMW polyethylene (Very High Molecular Weight polyethylene) polymer is a linear polyethylene with a molecular weight in the range of 500,000 to 3,000,000. UHMV & VHMV polyethylene offers the following characteristics, making it a superior polymer carrier for marine antifouling phytochemicals. It is the highest abrasion resistance of any thermoplastic polymer, outstanding impact strength even at very low temperatures, an excellent sliding material due to the low coefficient of friction, self-lubricating (non-caking and sticking), good chemical and stress cracking resistance and FDA and USDA approved. These compositions are low maintenance.

The compositions of the invention may further comprise control release agents such as, for example, micro-encapsulation of the phytochemicals to maintain sustained and prolonged release of the biocidal agents at the treated surface. The present invention also provides compositions which may comprise at least one biocidal phytochemical, wherein the phytochemical(s) may be microencapsulated using any of, or a combination of different types of coating materials. The selection of the appropriate coating material will depend on the application for the use of biocidal phytochemical agents. For example, the coating material must be resistant to the encapsulated phytochemical(s) and not, for example, readily dissolved by them. When used in architectural paints & coatings, and marine paints the microcapsule coatings advantageously will be resistant to dissolution in the medium of the paint or coating or selected so as to release the active phytochemical agent over a prolonged period. Those coatings to be included in for aquaculture system and polymers used in food wrap and food containers that may encounter an aqueous environment may be selected so as to provide prolonged release of the agents to the surrounding water or upon contact by biological organisms. Wood treatment coatings & processes, filter membranes, and latex urinary indwelling catheters may be treated with compositions according to the present invention that include microencapsulated phytochemicals for controlled time release of the biocidal phytochemicals, control or mask the taste or odor of the phytochemicals where needed, protect the biocidal phytochemical from extreme heat during the manufacturing process, slow down oxidation from exposure and extend the active efficacy of the biocidal phytochemical.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION

Figure 1A:
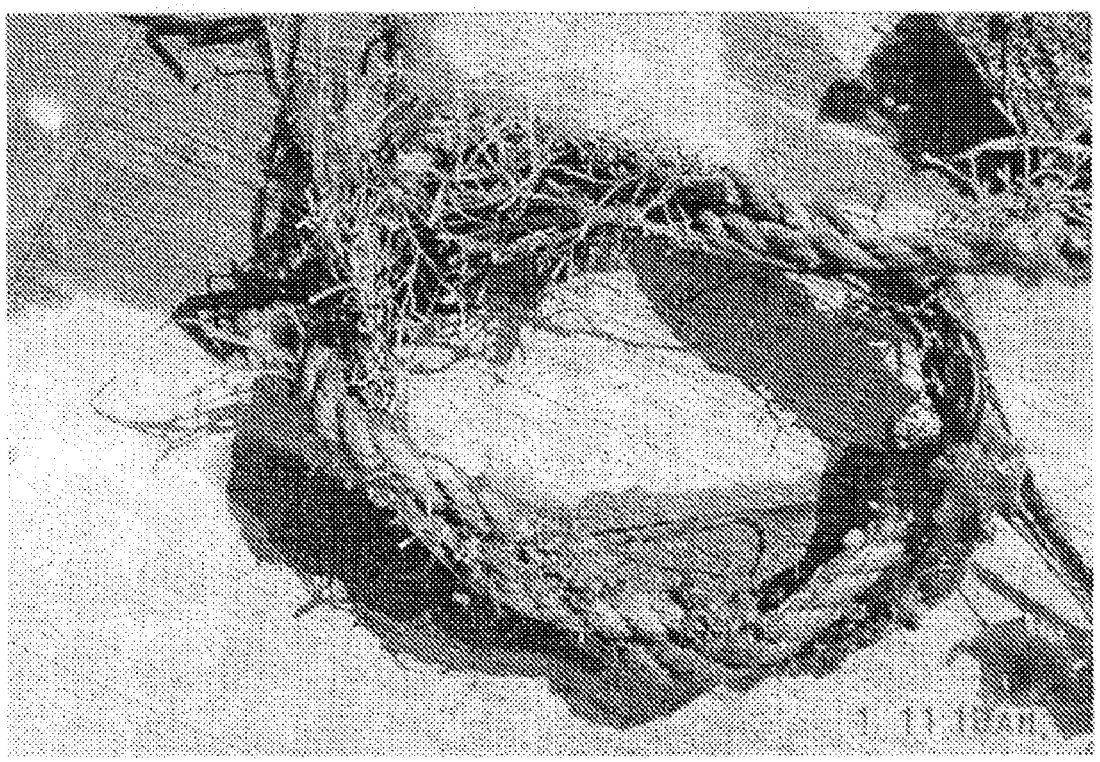
FIG. 1A illustrates thefouling on submerged rope with five (5) months immersion.

The term 'phytochemical' includes naturally occurring phytochemical molecular constructions, derivatives thereof, functional moieties thereof, and functionally identical manufactured molecular constructions as may be obtained based upon the naturally occurring compositions herein described. The term "phytochemical" as used herein may refer to a compound or combination of compounds isolated from botanical sources and which may be incorporated in the present invention as biocides including, but not limited to, *Jasonia candicans* (sesquiterpenes, lactones); *Polygonum flaccidum* (flavone and alpha santalene derivatives); *Acalypha wikesiana* (extracts); *Pavetta owariensis* (procyanidins); *Plectranthus hereroensis* (diterpenoids, diterpenes); Moss (Dicranin extract); *Cannabis sativa* (extract); *Gloiosiphonia* spp. (gloiosiphones); *Laminaceae* spp. (extract); *Securidaca* spp. (extract); *Veronia* spp. (extract); *Hyptis umbrose* (umbrosone); *Asclepias syriaca* (milkweed extract); *Tagetes tenuifolia* (thiophene); *Calophyllum inophylloide* (flavonoids); *Tanacetum densum* (sesquiterpene lactones, triterpenoids); *Neorautanenia mitis* (extract); *Premna schimper* (diterpene); *Premna oligotricha* (sesquiterpenes); *Premna oligotricha* (diterpenes); *Jasonia candicans* (essential oils); *Visnea mocanera* (beta-sitosterol, triterpenic betulinic acid, ursolic acid, plantanic acid); *Asteraceae* spp. (terthiophenes and polyynes); *Petalostemum purpureum* (extract); *Camelia sinensis* (catechin); *Helichrysum picardii* (flavonoids); *Helichrysum italicum* (flavonoids); *Corydalis pallida* (protoberberine alkloids); *Shiraia bambusicola* (perylenequinones); *Fraxinum omus* (hydroxycoumarins); *Podocarpus nagi* (totarol and nortiterpene dilactones); *Heterotheca inuloides* (sesquiterpenoids); *Pelargonium* spp. (essential oils); *Piper sarmentosum* (phenylpropanoids); *Allium* spp. (extract); *Juniperus procera* (diterpenes); *Achillea conferta* (flavonoids, flavones, sesquiterpenoid lactones); *Magnolia virginiana* (lignans, neolignans); *Eucalyptus euglobal* (euglobal); *Armillaria mellea* (armillaric acid); *Dracena mannii* (spirostanol saponin); *Piper aduncum* (chromenes, prenylated benzoic acid); *Rhamnaceae* spp. (cyclopeptide alkaloids); *Buddleja globosa* (verbascoside); *Cephalocereus senilis* (phytoalexin aurone); *Salvia albocaerulea* (diterpene); *Gomphrena martiana* and *Gomphrena boliviana* (extracts); *Paepalanthus* spp. (vioxanthin); *Helichrysum stoechas* and *Helichrysum crispum* (extracts); *Achillea ptarmica* (trans-pinocarveyl hydroperoxides); *Dehaasia incrassata* (alkaloids); *Asteraceae* spp. (extracts); *Arctotis auriculate* (extracts); *Eriocephalus africanus* (extracts): *Felicia erigeroides* (extracts); *Hemerocallis fulva* (phytosterols, fatty acid esters); *Psoralea juncea* (plicatin B); *Pluchea symphytifolia* (caffeic acid esters); *Tovomitopsis psychotrifolia* (Vitamin E derivative); *Celosia argentea* (triterpenoid saponins and flavonoids); *Azadirachta indica* (tetranortriterpenoid, mahmoodin, protolimonoids, naheedin); *Moraceae* spp. (coumarins);

*Hypericum erectum* (phloroglucinol derivatives); *Podospora appendiculate* (Appenolides A, B, & C, furanones); *Artemisia princeps* var. *orientalis, Artemisia capillaris, Artemisia mexicana* and *Artemisia scoparia* (extract); Paddy malt (mash extract); *Kigelia pinnata* (extract); *Acalypha wilkesiana* (extract); seaweeds, seagrass and lemongrass (essential oils); *Borrieria latifolia, Borreria setidens, Hedyotis diffusa), Hedyotis nudicaulis, Morinda elliptica, Morinda umbellata, Sida rhombifolia*, and *Vitex ovata* (extracts); *Tabebuia impetiginosa, Achyrocline* spp., *Larrea divaricata, Rosa borboniana, Punica granatum, Psidium guineense, Lithrea ternifolia* (extracts); *Lepechinia caulescens, Lepidium virginicum* and *Tanacetum parthenium* (extracts); *Talaromyces flavus* (extracts); *Daucus carota* (extract); *Flabellia petiolata, Caulerpa prolifera, Halimeda tuna, Corallina elongata, Lithophyllum lichenoides, Phyllophora crispa, Cystoseira* spp., *Halopteris* spp., *Codium* spp., *Valonia utricularis, Posidonia oceanica, Zostera nolti* and *Cymodocea nodosa* (extracts); *Centauraea orientalis, Diospyros khaki, Sida hermaphrodita, Forsythia intermedia, Scutellaria polydon, Eugenia malaccensis* and *Eugenia jambolana* (extracts); *Fritillaria* L. spp. (ebeinone, steroidal alkaloids); *Kigelia pinnata, Peperomia pellucida, Populus nigra, Populus balsamifera* and *Populus deltoides* (extracts); *Melaleuca alternifolia* (essential oil); *Elfvingia applanata* (naringenin); *Ficus sycomorus*, grapefruit seed, Garlic, Allicin, Peat, *Strophanthus hispidus, Secamone afzeli, Mitracarpus scaberi, Entada abyssinjca, Terminalia spinosa, Harrisonia abyssinica, Ximinea caffra, Azadirachta indica, Spilanthes mauritiana, Terminalia spinosa* (extracts); Cyanobacteria (ambigols A and B, tjipanazole); coffee (extract); *Sporochnus pedunculatus, Dalbergia melanozylon, Celastrus scandens, Juglans nigra, Kalmia latifolia, Pelargonium xhortorum, Rhus glabra* and *Lindera benzoin* (extracts); *Striga densiflora, Striga orobanchioides, Striga lutea, Pistacia lentiscus* L., *Mitracarpus villosus, Bixa orellana, Bridelia ferruginea, Alpinia katsumadai, Alpinia officinarum, Artemisia capillaris, Casia obtusifolia, Dendrobium moniliforme, Epimedium grandiflorum, Glycyrrhiza glabra, Lithosperum erythrorhizon, Magnolia obovata, Morus bonbycis, Natopterygii incisium, Polygonum multiflorum, Prunus mume, Rheum palmatum, Ricinus communis, Sophora flavescens, Swertia japonica*, black pepper, rosemary, red pepper, *Isopyrum thalictroides, Calotropis procera, Chrysanthemum* spp., *Holarrhena antidysenterica, Lunularia crusiata, Dumertiera hirsuta, Exormotheca tuberifera*, and liverwort (extracts); *Filipendula ulmaria, Salix glauca, Usnea filipendula, Clkadina arbuscula* (salicylic compounds); *Tanacetum parthenium, Thymus capitatus*, and *Elfngia applanata* (extracts); *Fraxinus ornus* (hydroxycoumarins, esculin, esculetin, fraxin, and fraxetin); *Zizyphus nummularia*, LONGO VITAL, *Pelargonium* spp., *Scaevola sericea, Psychotria hawaiiensis, Pipturus albidis, Aleurites moluccana, Solanum niger, Piper methysticum, Barringtonia asiatica, Adansonia digitata, Harungana madagascariensis, Jacaranda mimosaefolia, Erythroxylum catauba, Bidens pilosa, Lemna minor, Potamogeton* spp., *Nasturtium officinale, Apium nodiflorum, Agaricus subrutilescens, Amanita virosa, Amanita pantherina, Lycoperdon perlatum, Psidium guajava, Averrhoa carambola, musa sapientum, Carica papaya, Passiflora edulis, Lansium domesticum* and *Baccaurea motleyana* (extracts); horse radish, celandine grass, bur marigold and yarrow grass (extracts); *Abuta grandifola, Cyperus articulatus, Gnaphalium spicatum, Pothomorphe peltata, Ficus sycomorus, Ficus Benjamina, Ficus bengalensis, Ficus religiosa, Alchomea cordifolia, Bridelia feruginea, Eucalyptus citriodora, Hymenocardia acida, Maprounea africana, Monachora arbuscula, Tedania ignis, Arenosclera* spp., *Amphimedon viridis, Polymastia janeirensis, Aplysina fulva, Pseudaxinella lunaecharta, Nelumbium speciosum* and *Mycale arenosa* (extracts); cloves (eugenol acetate and isoeugenol); *Chrysthanemum boreale* (sesquiterpenoid lactones); *Eucalyptus globolus, Punica granatum, Bocconia arborea, Syzygium brazzavillense, Syzygium guineense, Carthamus tinctorius), Ginkgo biloba, Mosla chinensis, Salvia officinalis*, and *Cinnamomum cassia* (extracts); *Cryptolepis sanguinolenta* (alkaloids, cryptolepine); *Chelidonium majus* (alkaloids, berberine, coptisine); *Vitex agnus-castus* (extract); *Cladonia substellata* (usnic acid); Ellagic acid, *Fuligo septica, Tubifera microsperma* (extract); *Mundulea monantha, Tephrosia linearis* (flavonoids); *Lpomoea fistulosa* (extract); *Pimenta dioica* (essential oils); *Ratibida latipalearis, Teloxys graveolens, Dodonaea viscosa, Hypericum calycinum, Hyptis albida, Hyptis pectinata, Hyptis suaveolens* and *Hyptis verticillata* (extracts); *Asteriscus graveolones* (bisabolone hydroperoxides); *Derris scandens, Alnus rubra*, Araliaceae family (extracts); *Vinca rosea*, Australian tea tree oil, peppermint oil, sage oil, thymol, eugenol and *Thuja orientalis* (extracts); *Anacardium occidentale* (phenolic lipids); *Oidiodendron tenuissimum* (extract); *Acacia nilotica* and *Acacia farnesiana* (polyphenol, tannin); *Teminalia alata* and *Mallotus phillipinensis* (extracts); *Piectranthus grandidentatus* (abientane diterpenoids); *Pumica granatum* and *Datura metel* (extracts); tea, *Agave lecheguilla, Chamaesyce hirta, Baccharis glutinosa* and *Larrea tridentata* (extracts); *Camelia sinensis* and *Euphorbia hirta* (theaflavin, polyphenon 60); *Tabernaemontana pandacaqui, Yucca shidigera, Hemistepa lyrata, Yougia japonica, Prunella vulgaris, Lamium amplexicaule, Juniperus chinensis, lxeris dentata, Gnaphalium affine, Chelidonium majus, Spirea prunifolia, Erythronium japonicum, Taxus wallichiana, Ganoderma lucidum Drava nemorosa, Youngia capillaris, Equisetum arvense*, Australiam Lavender, Black Seed, *Catuaba casca, Cineole, Damiana, Dicranum scoparium, Eucalptus* oil, Ginger, and Grape seed (extracts); Neem seed, bark, and leaf extract; Neem oil; New Zealand Manuka extract; *Nicotiana tabacum* extract; olive leaf extract; a-pinene and b-pinene extracts; Rhubarb root extract; *Syringa vulgaris* extract; Tea tree oil (Terpinen-4-ol, a-terpinene, y-terpinene, a-terpineol, Terpinolene); Thyme (extract) and Vitamin E (extract).

The term "polymer base" as used herein refers to any polymer composition suitable for admixing with the antifouling compositions of the present invention and which may be used for the coating of a pre-existing structure or as a structural material for equipment, or components thereof that are in a moist or submerged environment. Paint, for example, may comprise a mixture of a polymeric primer and a suitable solvent or suspension medium. It will be understood by one of skill in the art that a paint base may be suitable for application to the submerged hull of a ship or boat (a marine paint base) and/or to the surface of, for example, a building or article of furniture and will provide a durable coating thereof. The paint may be an ablative paint wherein the immediate outer surface of the applied paint coating may be removed by frictional forces as a hull moves through water. The ablation will contribute to the removal of any colonizing organisms, as well as maintain the effective concentration of the biocidal phytochemical at the immediate surface. The term "polymer base" as used herein may further refer to a coating material other than a paint such as, but not limited to, a latex base. UHMV & VHMV polyethylene and other types of compression molding and latex compounds. UHMV (Ultra High Molecular Weight) polyethylene polymer is a linear polyethylene with a molecular weight in the range of 3,000,000 to 10,000,000. This value represents the "average molecular weight". Therefore, UHMW polymers have a molecular weight average 10 times that of conventional high density polyethylene resins. The higher molecular weight is what gives UHMW polymers a unique combination of characteristics making it more suitable for many applications where lower molecular weight grades fail. VHMW polyethylene (Very High Molecular Weight polyethylene) polymer is a linear polyethylene with a molecular weight in the range of 500,000 to 3,000,000. UHMV & VHMV polyethylene offers the following characteristics, making them suitable polymer carriers for marine antifouling phytochemicals. It has the highest abrasion resistance of any thermoplastic polymer, outstanding impact strength even at very low temperatures, an excellent sliding material due to the low coefficient of friction, self-lubricating (non-caking and sticking), good chemical and stress cracking resistance and FDA and USDA approved. These compositions are low maintenance. It is contemplated, however, that any polymer may be admixed with compositions of the invention, wherein the polymer is suitable for manufacturing components of, for example, aquaculture apparatus.

The term "primer" as used herein refers to, but is not limited to, chlorinated natural rubber primer, epoxy resin primers, silicone elastomer primer, and epoxy polysiloxane.

The term "resin" as used herein refers to, but is not limited to, polysulfonates, silyl ether polymers, and polyphosphates, polyethyle resins, epoxy resins and the like.

The term "pigment" as used herein refers to, but is not limited to, calcium carbonate, zinc oxide, iron oxide, and color pigments.

The term "solvent" as used herein refers to, but is not limited to, xylene, methyl iso-butyl ketone, other organic solvents including, but not limited to, acetone, turpentine and synthetic paint solvent. An acrylic based paint or medium may have as a solvent an aqueous based medium that may comprise other solvents including, for example, isopropanol.

The terms "binder" as used herein refers to, but is not limited to, rosins, resins, acrylic siloxine, acrylic-siloxine graft copolymers, calcium carbonate, siloxanes, silicones, silylacrylates, hydrolysable; trimethylsilyloxyethyl methacrylate copolymer; the copolymers, methyl acrylate, methyl methacrylate, styrene, lauryl methacrylate, vinyl acetate, vinyl chloride, acrylate copolymer paint binders and ester terminated silicones.

The term "anti-settling agent" as used herein refers to, but is not limited to, polyamide wax, paraffin waxes and hydrocarbon waxes.

The term "marine" as used herein refers to any aqueous environment including sea and freshwater either in the open environment such as the ocean, a lake or river, or any other extensively submerged surface such as the lining of a pipe or the inner surface of a fish tank, for example.

The term "active concentration" as used herein refers to the concentration of the antifouling agents available for control of organism growth on surfaces below the water. For application in ablative paint (coatings), self-polishing coatings, longlife coatings and fouling release coatings of the present invention, using antifouling agents according to the invention and either alone or in combination, with or without migration control agents, active concentration levels of the biocidal phytochemical concentrations will repel or inhibit the growth of marine organisms on underwater surfaces that are safe for the environment.

The present invention is directed to antifouling compositions and to polymers containing said antifouling agents and methods of making and using the same. The compositions of the present invention are effective against marine and/or freshwater organisms capable of attaching to and colonizing the submerged surfaces of aquaculture equipment including cages, ropes and the like and the submerged surfaces of ships and boats, including parazoans, coelenterates such as polychaete and oligochaete worms, molluscs, arthropods including crustaceans such as, but not limited to, acorn and goose barnacles and to be effective in inhibiting the attachment and or development of the adult or larval forms of the targeted organisms. The antifouling compositions of the present invention can also be effective against marine and freshwater plants including diatoms, algae and higher plants that can attach to a submerged surface and may inhibit or otherwise effectively reduce the formation of biofilms to which colonizing organisms may attach. It is intended, however, that the compositions of the invention may also be effective at preventing or inhibiting the biocolonization of any surface including surfaces not immersed in water, marine or fresh.

One aspect of the present invention provides environmentally friendly antifouling compositions comprising at least one phytochemical effective in reducing or inhibiting the colonization of a surface by a fouling organism.

Antifouling agents especially useful in the present invention include, but are not limited to, *capsicum*, menthol, tea tree oil, grapefruit seed extract, pomegranate extract, vitamin E, and any phytochemical exhibiting biocidal activity that does not present an environmental danger, as well as proteinases, such as but not limited to, bromelain and trypsin, and used in any combination.

The rate of migration or the release of the antifouling compositions admixed within marine paints, coatings and polymers may be modified by further including in the compositions a release agent such as Vitamin E, a chemical releaser such as citric acid, or an anti-oxidant such as Vitamin E. The chemical releaser may be the same as the phytochemical agent. Vitamin E further possesses antimicrobial properties, and thus can itself function as a biocidal phytochemical, which may work in conjunction with or separately from marine paint binders. Other antioxidants that may be useful in the present invention include, but are not limited to, lysine, butylatedhydroxytoulene (BHT), butylatedhydroxyanisole (BHA), grape seed extract, Pine bark extract (Proanthocyanidins), β-carotene, bilberry extract, ascorbic acid, *Ginkgo biloba* extract, green tea extract, tumeric, zinc picolinate, zinc oxide, iron oxide, calcium carbonate and selenium. Selected antioxidant(s) may be used alone or in combination when combined with the phytochemical(s) in the coating formulas of the present invention.

For applications using leaching paints (coatings), ablative paints (coatings) or self-polishing coatings (polymers such as latex polymers) wherein the antifouling compositions comprise the *capsicum*, tea tree oil, grapefruit seed extract, pomegranate extract, tannins, tannic acid, camphor, camphor oil, *Zostera noltil*, and/or menthol for their antimicrobial activity, with or without a migration release agent, the components of the leaching paints (coatings), ablative paints (coatings) and self-polishing polymers (coatings) may contain any combination of the primers, resins, pigments, solvents, paint binders and anti-settling agents known to those of skill in the art that provide effective application properties to, for example, the submerged region of a ship's hull.

The amounts of the biocidal agents added to the compositions may be adjusted according upon the particular application. Factors to consider are the conditions under which the composition is to be used, the microorganisms to be inhibited, the duration of the use, whether the object to be protected is a submerged, and the active concentration of the antimicrobial agents that is desired. For example, capsicum can be added in an amount from about 1 ppm to about 100,000 ppm, depending upon the desired application.

The embodiments of the present invention encompass an antifouling base composition comprising *capsicum*, menthol and tea tree oil. A formula for the antifouling base composition of the invention is presented in Example 7, Table 9 below. The present invention, however, further encompasses the incorporation of other antifouling agents with the first or base composition, including phytochemicals such as, but not limited to, pomegranate extract and grapefruit seed extract, as described, for example, in Examples 8 and 9 below.

The antifouling compositions of the invention may further comprise at least on protease. Suitable proteases for inclusion in the compositions advantageously retain proteolytic activity at the surface of the coated product ad are not significantly inactivated by any of the components either of the polymer base or the antifouling compositions. Suitable proteases include, but are not limited to, trypsin, bromelain, proteinase K, gelatinase, serine endoprotease and the like.

*Capsicum* as incorporated in the antifouling base composition is a food or food seasoning commonly known as "hot pepper." The active heat ingredient in *capsicum* is capsaicin which is a mixture of two unsaturated and three saturated homologs. This mixture is also referred to as capsaicinoids, and includes dihydrocapsaicin and nordihydrocapsaicin. The pungency of capsaicin (capsiacinoids) is measured in Scoville heat units and typically range from 60,000 to 1,500,000 heat units.

Figure 1B:
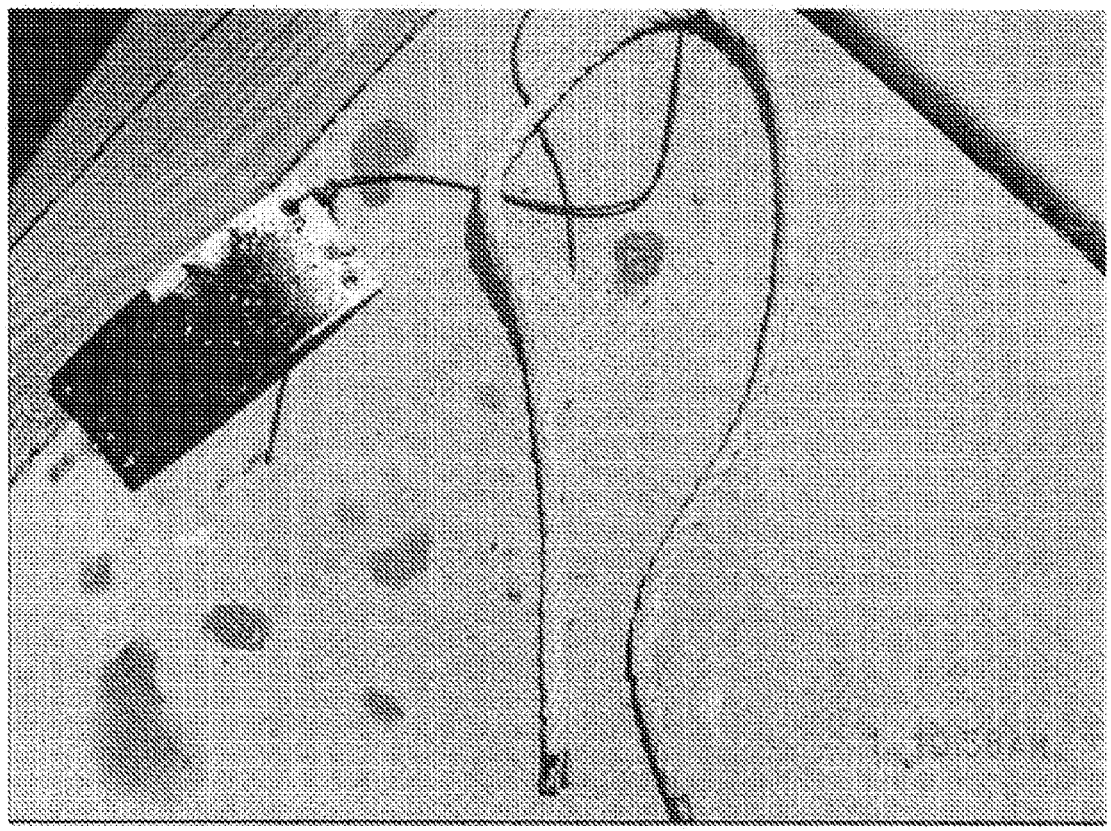
FIG. 1B illustrates the efficacy of coating a submerged rope with five (5) months immersion coated with a latex polymer incorporating antifouling compositions according to the invention to prevent the colonization of the rope with marine growth and FIG. 2 illustrates the efficacy of coating a submerged rope with nine (9) months immersion with a test sample aquaculture formula on far right.
Figure 2:
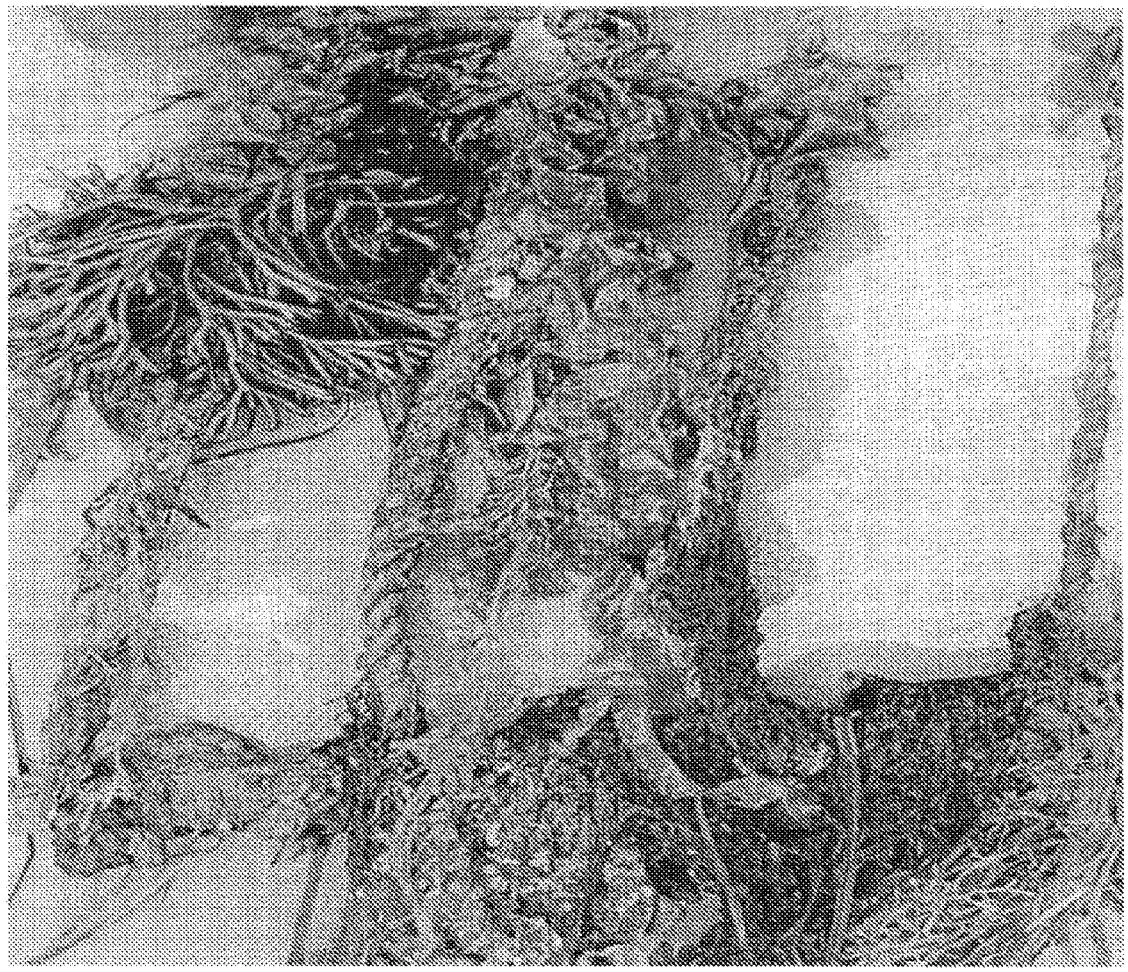

The antifouling base composition of the invention further comprises a menthol such as, but not limited to, mentholpropylreneglycolcarbonate. An example of a synthetic menthol preparation for inclusion in the compositions of the present invention is FRESCALIN™ (Symrise GmbH & Co, Holzminden, Germany) that comprises at least 50% by weight of isopulegol, between 25% and 49.99% by weight of 5-methyl-2-(1-methylethyl)-cyclohexanol and between 25% and 49.99% by weight of mentholpropylreneglycolcarbonate. This synthetic menthol preparation is effective in combination with *capsicum* at inhibiting marine growth when included in anti-fouling paints and coatings, as shown, for example in FIGS. 1A and 1B.

The compositions of the invention may further comprise pomegranate seed extract derived from *Punica granatum*, L. (punicaceae) used in whole or in part as fractions, including, but not limited to, the following active chemicals found in pomegranate 1,2,3,4,6-penta-o-galloyl-beta-D-glucose, 1,2,4,6-tetra-o-galloyl-beta-D-glucose, ascorbic acid, asiatic acid, betulinic acid, boric acid, casuarinin, chlorogenic acid, citric acid, corilagin, delphinidin-3-glucoside, elaidic acid, ellagic acid, ellagitannin, estradiol, estrone, freidelin, gallic acid, granatin-A, granatins, isopelletierine, linoleic acid, malic acid, malvidin, malvidin-pentose-gycoside, maslinic acid, neo-chlorogenic acid, niacin, oleic acid, oxalic acid, palmitic acid, pantothenic acid, pelletierine, phosphtidylcholine, polyphenols, protocatechuic acid, punicafolin, punicalain, punicalin, stearic acid, strictinin, tannin, ursolic acid. Pomegranate extract and certain prepared fractions are especially effective in combination with grapefruit seed extract at inhibiting marine growth when included in anti-fouling paints and coatings.

The compositions of the present invention may further include a chemical releaser, which is used to facilitate the controlled release of the antifouling agents from the polymer or paint matrix. The releaser may be, but is not limited to, citric acid, a phytochemical that also exhibits antibacterial activity. Zinc oxide, iron oxide or citric acid extract can be added to the polymer or paint (coatings) alone or in combination with other phytochemicals, with or without anti-oxidants like Vitamin E.

The amounts (by volume) and combinations (number) of the phytochemical agents added to the paints (coatings) may be adjusted according to the particular application, relevant factors including the conditions under which the phytochemical composition is to be used, the type of paint, coating or polymer (leaching, ablative, self-polishing), the thickness of the paint, coating or polymer, the rate of release of the phytochemical and the leach, ablation or polishing rate, the types of marine organisms that need controlling may vary, the duration of the use of the phytochemicals in these coatings, and the active concentration of the phytochemical desired. In some cases there may be a need for additional substances such as wetting or emulsifying agents, pH buffering agents, adjuvants, gelling or viscosity enhancing additives, preservatives, colors, and the like, depending upon the use.

The following antifouling agents may be used alone or in combination as biocidal compositions in coatings for aquaculture systems, marine paints, architectural paints, and coatings and the like: Grapefruit seed extract in an amount between from about 5% to about 40% w/v, pomegranate extract in an amount between from about 5% to about 40% w/v, menthol in an amount from about 5% to about 40% w/v, zosteric acid, (*Zostera noltil*), in amounts from about 5% to about 40% w/v, and *capsicum*, in an amount from about 0.05% to about 30% w/v. It is contemplated that the phytochemicals may be mixtures of compounds as extracted from the plant source material, or one or more of the biocidal agents isolated from the extract of the active ingredients and used in various combinations. It is further contemplated that in marine paint formulations for hull coatings, cuprous oxide in amounts from about 0.05% to about 25% w/v may be included to increase the overall biocidal activity of the paint. Preferably, however, this addition is avoided to prevent undesirable environmental harm.

An advantageous composition (hereinafter referred to as antifouling base composition) according to the invention comprises: (a) menthol at a concentration of between about 2% wet weight percent to about 20% wet weight percent; (b) *capsicum* at a concentration of between about 20% wet weight percent and about 80% wet weight percent; and (c) tea tree oil at a concentration of between about 2% wet weight percent and about 20% wet weight percent. An especially advantageous formula for the Antifouling Base Composition is: (a) menthol at a concentration of between about 12% wet weight percent; (b) *capsicum* at a concentration of about 75.5% wet weight percent; and (c) tea tree oil at a concentration of between about 12% wet weight percent as shown, for example, in Table 9 below.

Another composition (hereinafter referred to as antifouling composition No. 1) may be combined with the antifouling base composition and comprises: (a) pomegranate extract/grapefruit seed extract at a concentration of between about 50% wet weight percent and about 90% wet weight, wherein the pomegranate extract is about 90% volume/volume in propylene glycol and the grapefruit seed extract is about 10% volume/volume in glycerine; (b) bromelain at a concentration of between about 5% weight percent and 20% weight percent; (c) trypsin at a concentration of between about 2% weight percent and about 15% weight percent; and (d) vitamin E at a concentration of between about 0.05% weight percent and 5% weight percent. One advantageous embodiment of the Antifouling Composition No. 1 comprises (a) pomegranate extract/grapefruit seed extract at a concentration of about 81% weight percent, wherein the pomegranate extract is about 90% volume/volume in propylene glycol and the grapefruit seed extract is about 10% volume/volume in glycerine; (b) bromelain at a concentration of about 12% weight percent; (c) trypsin at a concentration of about 6% weight percent; and (d) vitamin E at a concentration of about 0.2% weight percent. An especially advantageous formulation of Antifouling Composition No. 1 is presented in Example 8, Table 10 below.

When incorporated into, for example, a latex base for coating an aquaculture apparatus, Antifouling Composition No. 1 may be combined with the Antifouling Base Composition, as shown, for example, in Table 11 below. When preparing such a mixture, the menthol, *capsicum* solution and the tea tree oil are warmed to dissolve the menthol before adding the remaining components such as those of Antifouling Composition No. 1. It is further contemplated that the Antifouling Base Composition and the Antifouling Composition No. 1 may be prepared without the addition of water, which can reduce transport costs. Water may then be added, if necessary, before mixing with a polymer base or by adding the antifouling composition according to the invention directly to a volume of water wherein the amount of the composition to be added maintains the effective concentrations of the antifouling agents. Adding of the antifouling compositions directly to water without mixing with polymers is particularly useful for the antifouling treatment of such as ballast waters of ships or their tanks before discharge into the ocean water. Therefore, embodiments of the invention may include compositions prepared without additional water.

Another aspect of the present invention provides durable polymeric compositions that may be liquid (such as paints) or solid (such as a polymeric coating of a catheter or food wrapping, comprising a paint or polymeric base and at least one antifouling composition.

When making any of the compositions of the present invention, the antifouling agents/compositions, antioxidants, and chemical releasers may be added either together or sequentially to marine paints, coatings and polymers. The mixture is then admixed until the antifouling agents are evenly dispersed within the paint, coating or polymer. The applications of the finished product may be brushed or sprayed on a surface to be coated, or as a dip coating or used to fabricate structures such as nets or ropes for use in aquaculture Phytochemicals that leach out of paint dilute and disperse extremely well into water and their biodegradability ensures they do not accumulate to unacceptable levels in the environment. Their antifouling effect particularly resides in a surface effect that takes place only in the immediate environment of the painted or coated surface. This characteristic makes the antifouling compositions of the present invention compatible with UHMW polyethylene and VHMW polyethylene, silicones, latex compounds and the like.

The present invention, therefore, also encompasses deposited polymer films that may be used to coat any fibrous material to prevent or inhibit the growth of organisms thereon. For example, glass fiber, hemp or a synthetic roping material or netting such as used in the aquaculture industry, may be pre-treated with a latex or other polymer coating incorporating the antifoulant compositions of the invention. For example, a rope material coated with a polymer coating, comprising biocidal phytochemicals according to the present invention resists colonization by marine organisms as shown, for example, in FIG. 1. There, a rope coated with isobutylene latex and including about 2.6% w/w grapefruit seed extract/pomegranate extract (1:1), 2% *capsicum* and 30% menthol, after 4 month immersion was void of marine growth compared to an untreated rope.

Treated glass-fiber may be used to form filters. The antifouling or biocidal coatings thereof according to the present invention will be able to prevent the growth of microorganisms, fungi and the like that may colonize the filter material during storage or use, especially under high humidity conditions.

A polymer base of particular use in the present invention is a latex composition that may be used to coat the surface of aquaculture equipment including, but not limited to, nets, cages buoys and ropes. For example, it is possible to use a latex polymers such as, but not limited to, an isoprene Isobutylene rubber (IIR) latex processed by prevulcanized BL-100 (IIR) latex compound with the following chemical formula: 10% PVA low viscosity, 60% zinc oxide dispersion, 68% sulfur dispersion, 50% butyl zimate slurry, 65% zetax dispersion and hodag PX 139.

However, the compositions of a latex base, as presented in Examples 1-6, are especially advantageous for impregnating the interstitial spaces of a multifiber rope, thereby coating most if not all of the fiber surfaces, and for application to nets and cages. When set, the latex polymer base provides a durable and flexible coating incorporating the antifouling compositions of the invention. The solution may be applied to a surface by any method known to one of skill in the art and adapted for the material to be coated. For example the surfaces or equipment may be coated by dipping, spraying, brush painting, or immersion in the antifouling polymer composition. The compositions of the invention may also be used to coat the exterior surfaces of cultivated mollusks such as oysters or mussels, thereby limiting the growth thereon of organisms which might slow the growth rate of the farmed shellfish either directly by overgrowing, or restricting the flow of clean water.

An advantageous synthetic latex base composition, as described in Examples 1-6 may comprise a polyurethane based thickener, at least one surfactant, at least one latex acrylic, a curing accelerator, and a cross-linker. For example, one advantageous composition of the latex polymer base comprises the surfactant COATOSIL™ 1211, the surfactant/wetting agent SILWET™ L-77, the latex acrylic NOVACRYL™-DP-126, the latex acrylic ACRYGEN™ 8662, cure accelerator ANCAMINE™ K-54, and the silicone/epoxy cross-linker COATOSIL™ 1770. Of the acrylic latexes, NOVACRYL™-DP-126 is a soft adhesive grade (20% of base polymers) and N-8662 is less tacky, tougher (80% of base polymers)—the weight-to-weight ratio of these two components may range from about 10:90 to about 60:10. Of the surfactants, C-1211 & L-77 add chemical and mechanical stability to the latex base and to the final antifouling composition, and reinforces the emulsification of the antifouling agents. Cross-linking of the acrylic latexes in this example is accomplished by using ANCAMINE™ K-54 & COATOSIL™ 1770 that effect cross-linking of the base polymers.

Optionally, in the latex base formulations for use in the present invention, ACRYSOL™ RM-825 is included when the mixture is dilute, i.e. 25% (for better stability & shelf life); at higher percentage solids of the final antifouling composition, i.e. 40-49%, less ACRYSOL™ RM-825 may be included to avoid excessive thickening; and may range from about 0.01% to about 5.0 weight percent of the dry latex solids.

For preparation of the antifouling compositions of the invention, diethyleneglycolbutylether, a coalescing (co-miscible) solvent may assist in keeping all of the anti-fouling agents in suspension in the latex polymer base and may be added to the latex base at a concentration of between about 5% weight/weight to about 30% weight/weight of the dry latex solids.

It is contemplated that the antifouling compositions of the invention may be incorporated into any polymer base that is suitable for coating or manufacturing an object that may be immersed in an aqueous environment. For example, in addition to a latex coating material as shown in Examples 1-6 below, the polymer base may be a durable solid such as, but not limited to, a polyethylene-based polymer useful for the construction of structures such as cages or ropes for the culturing of fish and other marine organisms, wherein the growth on the surface of the cages of fouling algae and sedentary organisms is undesirable. The bars of the cages, ropes and other items in contact with the marine environment, for example, may be of the polyethylene compositions comprising antifouling compositions of the invention that prevent the fouling growth from forming or surviving. Polyethylene (or other polymers such as PVC, porous nylon, cellulose, nitrocellulose and the like) polymer bases containing antifouling compositions according to the present invention may also be formed as porous sheets for use as filters such as reverse osmosis filters, which may be clogged by growth thereon of such as bacteria, algae or fungi during use.

One aspect, therefore, of the invention is antifouling marine coatings and materials using a high-molecular weight plastic such as, but not limited to, UHMV & VHMW polyethylene or other types of compression molding plastics. UHMV, Ultra High Molecular Weight polyethylene polymer is a linear polyethylene with a molecular weight in the range of 3,000,000 to 10,000,000. Very High Molecular Weight polyethylene polymer is a linear polyethylene with a molecular weight in the range of 500,000 to 3,000,000.

In the various embodiments of the paints and coatings of the present invention, biocidal phytochemicals of the present invention may be added in any combination to leaching paints (hard and soft), ablative paints (coatings), self-polishing coatings (polymers), long life antifouling coatings and fouling-release coatings at levels of at least 0.001% to about 60% by weight. In some cases cuprous oxide may be added in amounts from 0.05% to 30% ww/vv.

In various embodiments of the invention, the phytochemical *capsicum* is combined with a menthol and tea tree oil and optionally one or more other biocidal agents and added to a marine paint or polymer coating to control marine fouling.

In other embodiments of the invention, the phytochemical *capsicum* is combined with a menthol, tea tree oil and optionally one or more other biocidal phytochemicals and added to an architectural paint or polymer coating to control marine fouling. Tea tree oil is a natural by-product of the tea tree, (*Melaleuca* spp). Tea tree oil is extracted through natural non-toxic processes such as steam. Tea tree oil exhibits anti-fungal and anti-bacterial activity. Tea tree oil may be added to marine paints in combination with other phytochemicals, releasers like citric acid, or antioxidants like Vitamin E.

In various embodiments of the present invention, the antifouling compositions may further comprise at least one protease. In embodiments of the invention, the protease may be selected from the group consisting of bromelain, trypsin, proteinase K, a serine protease or a peptidase. In an advantageous embodiments the antifouling compositions may comprise a combination of bromelain and trypsin.

In one embodiment, the phytochemical, *capsicum* is combined with other a menthol, tea tree oil and optionally with one or more phytochemicals and added to marine paint to control marine fouling, wherein the *capsicum* is substantially free of the heat causing ingredient capsaicin.

In embodiments of the invention, a paint or coating comprises a polymer base, grapefruit seed extract, a menthol and *capsicum*.

In another embodiment of the invention, the antifouling compositions may include grapefruit seed extract, which exhibits anti-bacterial, anti-parasitic, and anti-fungal activity. The grapefruit seed extract can be added to architectural and marine paints alone or in combination with other phytochemicals, or in combination with antioxidants such as Vitamin E. The phytochemical grapefruit seed extract may be added to paint (coatings) to control marine fouling. In one embodiment of the invention, the grapefruit seed extract may be processed into a concentrated state and the glycol substantially removed from the extract before adding to marine paint or coating.

In other embodiments, the antifouling compositions may comprise pomegranate extract prepared from the rind, seed, pulp, leaf or bark or a combination of any of those plant parts used alone or in combination with any other phytochemical.

In another embodiment, the phytochemical may comprise pomegranate extract and grapefruit seed extract.

In another embodiment, the phytochemical may include various fractions of the active ingredients of pomegranate extract and grapefruit seed extract combined with menthol and *capsicum*.

The antifouling base compositions of the present invention may comprise *capsicum* having between about 100,000 Scoville units to at least 3,000,000 Scoville units, tea tree oil, and menthol or a derivative thereof.

In embodiments of the paints and coatings of the present invention, antifouling compositions of the present invention may be added in any combination to leaching paints (hard and soft), ablative paints (coatings), self-polishing coatings (polymers), longlife antifouling coatings and fouling-release coatings, at levels from about 0.1% to about 60% by volume.

In other embodiments of the paints and coatings of the present invention, phytochemicals of the present invention may be added in any combination to leaching paints (hard and soft), ablative paints (coatings), self-polishing coatings (polymers), longlife antifouling coatings and fouling-release coatings, at levels from about 0.001% to about 40% by volume.

In embodiments of the paints and coatings of the present invention, phytochemicals of the present invention may be added in any combination to leaching paints (hard and soft), ablative paints (coatings), self-polishing coatings (polymers), longlife antifouling coatings and fouling-release coatings, at levels from about 10% to about 60% by volume.

In the various embodiments of the paints and coatings of the present invention, phytochemicals may be added in any combination to any type of leaching paints (coatings) (hard and soft), ablative paints (coatings), self-polishing coatings (polymers), the ablative and self-polishing paints further comprising a primer, a resin, a pigment, a solvent, a paint binder and an anti-settling agent The present invention also provides coating compositions comprising environmentally benign phytochemicals suitable for use in preventing the colonization of a treated surface by various biological species on materials used in the aqua culture industry. Aqua culture is the business of the regulation and cultivation of water plants and animals for human use or consumption. There is a tremendous build up of marine fouling on the materials used in aqua culture, such as, ropes, nets, buoys, cages, traps, etc., which is costing the industry billions of dollars annually through labor intense maintenance to clean these materials. There is a need for a nontoxic antifouling coating and for the aqua culture industry to reduce the labor intense problem of cleaning fouling from aqua culture equipment.

The polyethylene-based compositions of the invention are also useful for the construction of such structures as cages for the culturing of fish and other marine organisms wherein the growth on the surface of the cages of fouling algae and sedentary organisms is undesirable. The bars of the cages, ropes and other items in contact with the marine environment, for example, may be of the polyethylene compositions comprising biocidal phytochemicals that prevent the fouling growth from forming or surviving.

Polyethylene (or other polymers such as porous nylon, cellulose, nitrocellulose and the like) biocidal compositions containing phytochemicals according to the present invention may also be formed as porous sheets for use as filters such as reverse osmosis filters which may be clogged by growth thereon of such as bacteria, algae or fungi during use.

One aspect, therefore, of the invention is antifouling marine coatings using UHMV & VHMW polyethylene and other types of compression molding. UHMV, Ultra High Molecular Weight polyethylene Polymer is a linear polyethylene with a molecular weight in the range of 3,000,000 to 10,000,000. Very High Molecular Weight polyethylene Polymer is a linear polyethylene with a molecular weight in the range of 500,000 to 3,000,000 as shown, for example, in Table 1 below

TABLE 1

| PROPERTY | ASTM TEST | UNITS METRIC (U.S.) | .030" | .060" | .125" |
|---|---|---|---|---|---|
| \multicolumn{6}{c}{UHMW MECHANICAL PROPERTIES} |
| Density | D792 | gm/cc | 0.93 | 0.93 | 0.93 |
| Tensile Strength @ Yield | D638 | MPa(psi) | 23 (3300) | 20 (2964) | 22 (3227) |
| Tensile Strength @ Break | D638 | MPa(psi) | 53 (7740) | 49 (7056) | 44 (6373) |
| Elongation @ Break | D638 | % | 460 | 463 | 466 |
| Youngs "E" Modulus | D638 | MPa(psi × 105) | 725 (1.05) | 731 (1.06) | 672 (0.97) |
| Izod Impact Strength (23° C.) | D256(1) | J/m(ft-lb/in notch) | | | |
| Izod Impact Strength (−40° C.) | D256(1) | J/m(ft-lb/in notch) | | | |
| Hardness Shore "D" | D2240 | — | 65 | 65 | 65 |
| Abrasion Resistance | | | | | |
| Water Absorbtion | D570 | % | Nil | Nil | Nil |
| Relative Solution Viscosity | D4020 | Dl/gm | 2.3-3.5 | 2.3-3.5 | 2.3-3.5 |
| COEFFICIENT OF FRICTION | | | | | |
| Static | | | 0.16 | 0.16 | 0.16 |
| Dynamic | | | 0.14 | 0.13 | 0.14 |

(1)Izod Impact Strength: Samples have two(15o +/− 1/2o) notches on opposite sides to a depth of 5 mm.

These Polyetheyenes have to be applied using rubber, silicone or acrylic adhesives that have the following properties and characteristics.

| Adhesion, 180i Peel | 2 mil | (0.05 mm) | Polyester Support |
|---|---|---|---|
| | U.S. POUNDS FORCE PER INCH WIDTH | METRIC NEWTONS PER METER | |
| Substrate: Stainless Steel (Applied One Minute) | 175 | 1975 | |
| \multicolumn{4}{c}{LOOP TACK} |
| Substrate: Stainless Steel | 288 | 3135 | |
| \multicolumn{4}{c}{STATIC SHEAR} |
| Temperature | Area | Load | Minutes to Failure |
| 72i F.(22i C.) | 1"(6.5 cm2) | 5.5 lbs(2.5 kg) | >10,000 |

| FEATURES | BENEFITS | STORAGE, SHELF LIFE & TEMP. INFO | SURFACE PREPARATION |
|---|---|---|---|
| Polypropylene Carrier | Stability in Processing | One year when stored at 70i F.(21i C.) | It is essential, as with all pressure-sensitive tapes, that the surface to which the tape is applied be clean, dry, and free of grease and oil. |
| Specially Formulated Adhesive | Combines high tack and adhesion with excellent shear | Minimum Application Temperature: 50i F.(10i C.) Maximum Continuous Temperature: 120i F.(49i C.) Maximum Intermittent Operating Temperature: 175i F.(79i C.) | |

One aspect, therefore, of the invention is antifouling marine coatings using latex. As an example; Isoprene Isobutylene Rubber (IIR) latex processed by prevulcanized BL-100 (IIR) latex compound with the following chemical formula: 10% PVA low viscosity, 60% zinc oxide oleporsion, 68% sulfur dispersion, 50% butyl zimate slurry, 65% zetax dispersion and hodag PX 139. Inert fillers may be used to improve the overall strength of the latex such as clays, talcs or silicates, which may offer a better transport route for the phytochemicals and reduce costs.

The following is a list, as examples, of phytochemicals: *Helichrysum italicum* (flavonoids); *Corydalis pallida* (protoberberine alkloids); *Shiraia babusicola* (perylenequinones); *Fraxinum omus* (hydroxycoumarins); *Podocarpus nagi* (totarol and nortiterpene dilactones); *Heterotheca inuloides* (sesquiterpenoids); *Pelargonium* spp. (essential oils); *Piper sarmentosum* (phenylpropanoids); *Allium* spp. (extract); *Juniperus procera* (diterpenes); *Achillea conferta* (flavonoids, flavones, sesquiterpenoid lactones); *Magnolia virginiana* (lignans, neolignans); *Eucalyptus euglobal* (*euglobal*); *Armillaria mellea* (armillaric acid); *Dracena mannii* (spirostanol saponin); *Piper aduncum* (chromenes, prenylated benzoic acid); *Rhamnaceae* spp. (cyclopeptide alkaloids); *Buddleja globosa* (verbascoside); *Cephalocereus senilis* (phytoalexin aurone); *Salvia albocaerulea* (diterpene); *Gomphrena martiana* and *Gomphrena boliviana* (extracts); *Paepalanthus* spp. (vioxanthin); *Helichrysum stoechas* and *Helichrysum crispum* (extracts); *Achillea ptarmica* (trans-pinocarveyl hydroperoxides); *Dehaasia incrassata* (alkaloids); *Asteraceae* spp. (extracts); *Arctotis auriculate* (extracts); *Eriocephalus africanus* (extracts): *Felicia erigeroides* (extracts); *Hemerocallis fulva* (phytosterols, fatty acid esters); *Psoralea juncea* (plicatin B); *Pluchea symphytifolia* (caffeic acid esters); *Tovomitopsis psychotrifolia* (Vitamin E derivative); *Celosia argentea* (triterpenoid saponins and flavonoids); *Azadirachta indica* (tetranortriterpenoid, mahmoodin, protolimonoids, naheedin); *Moraceae* spp. (coumarins); *Hypericum erectum* (phloroglucinol derivatives); *Podospora appendiculate* (Appenolides A, B, & C, furanones); *Artemisia princeps* var. *orientalis, Artemisia capillaris, Artemisia mexicana* and *Artemisia scoparia* (extract); Paddy malt (mash extract); *Kigelia pinnata* (extract); *Acalypha wilkesiana* (extract); seaweeds, seagrass and lemongrass (essential oils); *Borrieria latifolia, Borreria setidens, Hedyotis diffusa*), *Hedyotis nudicaulis, Morinda elliptica, Morinda umbellata, Sida rhombifolia*, and *Vitex ovata* (extracts); *Tabebuia impetiginosa, Achyrocline* spp., *Larrea divaricata, Rosa borboniana, Punica granatum, Psidium guineense, Lithrea ternifolia* (extracts); *Lepechinia caulescens, Lepidium virginicum* and *Tanacetum parthenium* (extracts); *Talaromyces flavus* (extracts); *Daucus carota* (extract); *Flabellia petiolata, Caulerpa prolifera, Halimeda tuna, Corallina elongata, Lithophyllum lichenoides, Phyllophora crispa, Cystoseira* spp., *Halopteris* spp., *Codium* spp., *Valonia utricularis, Posidonia oceanica, Zostera noltii* and *Cymodocea nodosa* (extracts); *Centauraea orientalis, Diospyros khaki, Sida hermaphrodita, Forsythia intermedia, Scutellaria polydon, Eugenia malaccensis* and *Eugenia jambolana* (extracts); *Fritillaria* L. spp. (ebeinone, steroidal alkaloids); *Kigelia pinnata, Peperomia pellucida, Populus nigra, Populus balsamifera* and *Populus deltoides* (extracts); *Melaleuca alternifolia* (essential oil); *Elfvingia applanata* (naringenin); *Ficus sycomorus*, grapefruit seed, Garlic, Allicin, Peat, *Strophanthus hispidus, Secamone afzeli, Mitracarpus scaberi, Entada abyssinjca, Terminalia spinosa, Harrisonia abyssinica, Ximinea caffra, Azadirachta indica, Spilanthes mauritiana, Terminalia spinosa* (extracts); Cyanobacteria (ambigols A and B, tjipanazole); coffee (extract); *Sporochnus pedunculatus, Dalbergia melanozylon, Celastrus scandens, Juglans nigra, Kalmia latifolia, Pelargonium xhortorum, Rhus glabra* and *Lindera benzoin* (extracts); *Striga densiflora, Striga orobanchioides, Striga lutea, Pistacia lentiscus* L., *Mitracarpus villosus, Bixa orellana, Bridelia ferruginea, Alpinia katsumadai, Alpinia officinarum, Artemisia capillaris, Casia obtusifolia, Dendrobium moniliforme, Epimedium grandiflorum, Glycyrrhiza glabra, Lithosperum erythrorhizon, Magnolia obovata, Morus bonbycis, Natopterygii incisium, Polygonum multiflorum, Prunus mume, Rheum palmatum, Ricinus communis, Sophora flavescens, Swertia japonica*, black pepper, rosemary, red pepper, *Isopyrum thalictroides, Calotropis procera, Chrysanthemum* spp., *Holarrhena antidysenterica, Lunularia crusiata, Dumertiera hirsuta, Exormotheca tuberifera*, and liverwort (extracts); *Filipendula ulmaria, Salix glauca, Usnea filipendula, Clkadina arbuscula* (salicylic compounds); *Tanacetum parthenium, Thymus capitatus*, and *Elfingia applanata* (extracts); *Fraxinus ornus* (hydroxycoumarins, esculin, esculetin, fraxin, and fraxetin); *Zizyphus nummularia*, LONGO VITAL, *Pelargonium* spp., *Scaevola sericea, Psychotria hawaiiensis, Pipturus albidis, Aleurites moluccana, Solanum niger, Piper methysticum, Barringtonia asiatica, Adansonia digitata, Harungana madagascariensis, Jacaranda mimosaefolia, Erythroxylum catauba, Bidens*

*pilosa, Lemna minor, Potamogeton* spp., *Nasturtium officinale, Apium nodiflorum, Agaricus subrutilescens, Amanita virosa, Amanita pantherina, Lycoperdon perlatum, Psidium guajava, Averrhoa carambola, musa sapientum, Carica papaya, Passiflora edulis, Lansium domesticum* and *Baccaurea motleyana* (extracts); horse radish, celandine grass, bur marigold and yarrow grass (extracts); *Abuta grandifola, Cyperus articulatus, Gnaphalium spicatum, Pothomorphe peltata, Ficus sycomorus, Ficus Benjamina, Ficus bengalensis, Ficus religiosa, Alchornea cordifolia, Bridelia feruginea, Eucalyptus citriodora, Hymenocardia acida, Maprounea africana, Monachora arbuscula, Tedania ignis, Arenosclera* spp., *Amphimedon viridis, Polymastia janeirensis, Aplysina fulva, Pseudaxinella lunaecharta, Nelumbium speciosum* and *Mycale arenosa* (extracts); cloves (eugenol acetate and isoeugenol); *Chrysthanemum boreale* (sesquiterpenoid lactones); *Eucalyptus globolus, Punica granatum, Bocconia arborea, Syzygium brazzavillense, Syzygium guineense, Carthamus tinctorius), Ginkgo biloba, Mosla chinensis, Salvia officinalis,* and *Cinnamomum cassia* (extracts); *Cryptolepis sanguinolenta* (alkaloids, cryptolepine); *Chelidonium majus* (alkaloids, berberine, coptisine); *Vitex agnus-castus* (extract); *Cladonia substellata* (usnic acid); Ellagic acid, *Fuligo septica, Tubifera microsperma* (extract); *Mundulea monantha, Tephrosia linearis* (flavonoids); *Lpomoea fistulosa* (extract); *Pimenta dioica* (essential oils); *Ratibida latipalearis, Teloxys graveolens, Dodonaea viscosa, Hypericum calycinum, Hyptis albida, Hyptis pectinata, Hyptis suaveolens* and *Hyptis verticillata* (extracts); *Asteriscus graveolones* (bisabolone hydroperoxides); *Derris scandens, Alnus rubra,* Araliaceae family (extracts); *Vinca rosea,* Australian tea tree oil, peppermint oil, sage oil, thymol, eugenol and *Thuja orientalis* (extracts); *Anacardium occidentale* (phenolic lipids); *Oidiodendron tenuissimum* (extract); *Acacia nilotica* and *Acacia farnesiana* (polyphenol, tannin); *Teminalia alata* and *Mallotus phillipinensis* (extracts); *Piectranthus grandidentatus* (abientane diterpenoids); *Pumica granatum* and *Datura metel* (extracts); tea, *Agave lecheguilla, Chamaesyce hirta, Baccharis glutinosa* and *Larrea tridentata* (extracts); *Camelia sinensis* and *Euphorbia hirta* (theaflavin, polyphenon 60); *Tabernaemontana pandacaqui, Yucca shidigera, Hemistepa lyrata, Yougia japonica, Prunella vulgaris, Lamium amplexicaule, Juniperus chinensis, lxeris dentata, Gnaphalium affine, Chelidonium majus, Spirea prunifolia, Erythronium japonicum, Taxus wallichiana, Ganoderma lucidum Drava nemorosa, Youngia capillaris, Equisetum arvense,* Australiam Lavender, Black Seed, *Catuaba casca, Cineole, Damiana, Dicranum scoparium, Eucalptus* oil, Ginger, and Grape seed (extracts); Neem seed, bark, and leaf extract; Neem oil; New Zealand Manuka extract; *Nicotiana tabacum* extract; olive leaf extract; a-pinene and b-pinene extracts; Rhubarb root extract; *Syringa vulgaris* extract; Tea tree oil (Terpinen-4-ol, a-terpinene, y-terpinene, a-terpineol, Terpinolene); Thyme (extract) and Vitamin E (extract).

Microorganisms which may be inhibited by biocidal phytochemicals useful in the present invention include, but are not limited to: Fungi, such as *Aspergillus flavus, A. fumigalus, A. niger, Blastomyces dermatitidis, Candida* spp., *Coccidioides immitis, Cryptococcus neoformans, Fusarium culmorum, Geotrichum* spp., *Histoplasma capsulatum, Malassezia furfur, Microsporum* spp., *Mucor racemosus, Nocardia* spp., *Paracoccidioides brasiliensis, Penicillium* spp., *Rhizopus higricans, Saccharomyces cerevisiae, Sporothrix schneckii, Torulopsis* spp., *Trichophyton* spp, Bacteria, such as *Aerobacter aerongenes, Aeromonas hydrophila, Bacillus cereus, Bacillus subtilis, Bordetella pertussis, Borrelia burgdorferi, Campylobacter fetus, C. jejuni, Corynebacterium diphtheriae, C. bovis, Desulfovibrio desulfurica, Escherichia coli* 0157:H7, Enteropathogenic *E. coli,* Enterotoxin-producing *E. coli, Helicobacter pylori, Klebsiella pneumoniae, Legionella pneumophila, Leptospira interrogans, Mycobacterium tuberculosis, M. bovis, Neisseria gonorrhoeae, N. meningitidis, Proteus mirabilis, P. vulgaris, Pseudomonas aeruginosa, Rhodococcus equi, Salmonella choleraesuis, S. enteridis, S. typhimurlum, S. typhosa, Shigella sonnei, S. dysenteriae, Staphylococcus aureus, S. epidermidis, Streptococcus anginosus, S. mutans, Vibrio cholerae, Yersinia pestis, Y. pseudotuberculosis, Actinomycetes, Stretomyces reubrireticuli, Streptoverticillium reticulum, Thermoactinomyces vulgaris,* Viruses, such as Adenoviruses, Coronaviruses, Cytomegalovirus, Enteroviruses, Epstein-Barr virus, Herpes simplex virus, Hepatitis viruses, Human Immunodeficiency virus, Human Parvoviruses, Influenza viruses, Morbillivirus, Mumps virus, Norwalk viruses, Papillomaviruses, Paromyxovirus, Poxvirus, Rabies virus, Reoviruses, Rotaviruses, Rubella virus, Respiratory Synctial virus, Rhinoviruses, Varicella zoster virus, Parasites such as *Ancyclostoma braziliense, Anisakis, Babesia microti, Balantidum coli, Blastocystis hominis, Chilomastix mesnili, Cryptosporidium parvum, Cyclospora, Dientamoeba fragilis, Diphyllobothrium latum, Echinococcus granulosus, Entamoeba coli, E. histolytica, Enterocytozoon, Fasciola hepatica, Giardia lamblia, Iodamoeba butschlii, Isospora belli, Leishmania brasiliensis, L. donovani, L. tropica, Paragonimus westermani, Plasmodium vivax, Pnemocystis carinii, Sarcocytis hominis, Strongyloides stercoralis, Taenia solium, Toxoplasma gondii, Trichomonas vaginalis, Trichinella spiralis, Trypanosoma cruzi.*

It is further intended that the compositions of the present invention will be effective against marine and/or freshwater organisms capable of attaching to and colonizing the submerged hull surfaces of ships and boats, including parazoans, coelenterates such as polychaete and oligochaete worms, molluscs, arthropods including crustaceans such as, but not limited to, acorn and goose barnacles and to be effective in inhibiting the attachment and or development of the adult or larval forms of the targeted organisms. The compositions of the present invention can also be effective against marine and freshwater plants including algae and higher plants that can attach to a ship hull and submerged aquaculture systems.

Exemplary phytochemicals that exhibit activity against multiple organisms useful in the present invention are illustrated in Table 2 below. Each phytochemical is classified as to general activity (anti-bacterial; anti-viral; anti-fungal; anti-crustacean; larvicidal; insecticidal; molluscicidal; or anti-nematodal) and specific examples of organisms against which the phytochemical is active are provided. However, it is to be recognized by one of ordinary skill in the art that the phytochemicals included in the table are provided for illustrative purposes only and are not meant to an exhaustive listing and with the recognition that certain phytochemicals may be active against more than one class of organism:

TABLE 2

| CLASSIFICATION | PHYTOCHEMICAL | TARGET ORGANISM |
| --- | --- | --- |
| Anti-bacterial | *Annona muricata* {Annonaceae} | *B. subtilis; E. coli* |
|  | *A. squamosa* | *B. subtilis* |
|  | *Panax ginseng* {Araliaceae} | *E. coli; P. aeruginosa; S. enteritidis* |
|  | *Capparis spinosa* {Capparidaceae} | *E. coli* |
|  |  | *B. subtilis; S. lutea; S. aureus* |

TABLE 2-continued

| CLASSIFICATION | PHYTOCHEMICAL | TARGET ORGANISM |
|---|---|---|
| | *Calendula officinalis* (Compositae) | *E. coli* |
| | | *S. aureus*** |
| | *Cynara scolymus* {Compositae} | *B. subtilis; B. mycoides; S. aureus; E. coli* |
| | *Cucurbita pepo* {Cucurbitaceae} | *E. coli* |
| | *Cymbopogon citratus* (Gramineae) | *B. anthracis; B. cereus; S. aureus; B. subtilis; P. aeruginosa; S. pneumoniae; Actinomycetes* |
| | *Mentha spicata* {Labiatae} | *B. subtilis; B. cereus; P. aeruginosa; S. typhi; S. aureus* |
| | *Ocimum basilicum* {Labiatae} | *B. subtilis; S. aureus; S. mutans* |
| | *Rosmarinus officinalis* {Labiatae} | *B. subtilis;*** H-17(rec+); C. perfringens; E. amylovora; E. coli; K. pneumoniae; X. campestris; P. aeruginosa; S. enteritidis; S. aureus; S. sanguis; E. carotovora* |
| | *Glycyrrhiza glabra* {Leguminosae} | |
| | *Allium sativum* (Liliaceae) | *B. subtilis; C. xerosis; P. vulgaris* |
| | *Aloe vera* {Liliaceae} | *E. coli; P. vulgaris; P. aeruginosa; S. mutans* |
| | *Citrus reticulata* {Rutaceae} | *S. mutans* |
| | *Oenothera biennis* {Onagraceae} | *S. dysenteriae* |
| | *Plantago major* {Plantaginaceae} | *B. anthracis; B. subtilis; E. coli;*** K. pneumoniae; P. aeruginosa; S. aureus* |
| | *Punica granatum* {Punicaceae} | *E. coli* |
| | *Ribes nigrum* {Saxifragaceae} | *Actinomycete sp.; B. pertussis; E. coli; P. shigelloides; P. aeruginosa; S. aureus; V. cholera* |
| | *Camellia sinensis* {Theaceae} | |
| | *Curcuma longa* {Zingiberaceae} | |
| | *Zingiber officinale* {Zingiberaceae} | *B. subtilis; L. acidophilus;* H-17(rec+) |
| | | *B. subtilis; B. anthracis; E. coli; L. acidophilus; S. aureus* |
| Anti-fungal | *Annona muricata* {Annonaceae} | *Penicillium oxalicum* |
| | *Panax ginseng* {Araliaceae} | *Rhizopus nigricans; Saccharomyces uvarum* |
| | *Capparis spinosa* (Capparidaceae) | *Candida pseudotropicalis* |
| | *Calendula officinalis* (Compositae) | *Neurospora crassa; Candida albicans; C. monosa* |
| | | *Neurospora crassa* |
| | *Cucurbita pepo* (Cucurbitaceae) | *Absidia spinosa; Alternaria solani; Aspergillus niger; Curvularia lunata; Epidermophyton floccosum; Microsporum audouini; Trichophyton mentagrophytes; Candida albicans; Cryptococcus neoformans; Saccharomyces cerevisiae* |
| | *Cymbopogon citratus* (Granimeae) | |
| | *Mentha spicata* (Labiatae) | |
| | *Ocimum basilicum* (Labiatae) | *A. niger; F. oxysporum; F. sp. Lentis;*** Trichophyton rubrum* |
| | *Rosmarinus officinalis* (Labiatae) | *Absidia ramosa;*** Alternaria longipes; Aspergillus aegyptiacus; A. awamori; Microsporum gypseum; Trichoconiella padwickii; C. albicans; Kloeckera apiculata F. oxysporum; M. icrosporum canis; P. cyclopium; C. albicans; Rhodotorula rubra; T. rubrum* |
| | *Glycyrrhiza glabra* (Leguminoseae) | |
| | *Allium sativum* (Liliaceae) | |
| | *Aloe vera* (Liliaceae) | *Aspergillus auricomus; T. mentagrophytes; C. albicans* |
| | *Sesamum indicum* {Pedaliaceae} | |
| | *Punica granatum* {Punicaceae} | *A. aegyptiacus;*** A. fumigatus; A. niger; Botryotrichum keratinophilum; E. floccosum; F. moniliforme; F. oxysporum; Geotrichum candidum; M. canis; Nannizzia fulva; Penicillium digitatum; T. rubrum; T. semii; C. albicans; C. krusei; C. pseudotropicalis; C. neoformans; Debaryomyces hansenii; Kloeckera apiculata; Rhizopus rhizopodiformis; T. padwickii* |
| | *Citrus aurantium* {Rutaceae} | |
| | *Citrus reticulata* {Rutaceae} | |
| | *Ribes nigrum* {Saxifragaceae} | |
| | *Camellia sinensis* {Theaceae} | |
| | *Curcuma longa* {Zingiberaceae} | |
| | *Zingiber officinale* {Zingiberaceae} | |
| | | *T. Mentagrophytes* |
| | | *Cladosporium cucumerinum* |
| | | *A. niger; C. albicans**** |
| | | *A. aegyptiacus;*** T. rubrum; C. albicans; C. lipolytica* |
| | | *A. niger; P. cyclopium; C. albicans* |
| | | *P. digitatum* |
| | | *E. floccosum; T. mentagrophytes; S. cerevisiae; Alternaria tenuis* |
| | | *Debaryomyces hansenii; A. flavus; A. niger; E. floccosum; Trichoderma viride* |
| | | *A. niger; A. auricomus; A. flavus; Botrytis cinerea; N. crassa; T. padwickii; C. albicans; S. pastorianus* |

TABLE 2-continued

| CLASSIFICATION | PHYTOCHEMICAL | TARGET ORGANISM |
|---|---|---|
| anti-viral | *Annona squamosa* (Annonaceae) | HIV-1 |
| | *Panax ginseng* {Araliaceae) | Adenovirus 3; herpes simplex 1 virus; |
| | *Capparis spinosa* (Capparidaceae) | semlicki-forest virus; rauscher murine leukemia virus |
| | *Calendula officinalis* (Compositae) | Hepatitis virus |
| | *Mentha spicata* (Labiatae) | Encephalitis virus-unspec.; herpes simplex virus; HIV-1 |
| | *Rosmarinus officinalis* (Labiatae) | Herpes virus type 2 |
| | *Glycyrrhiza glabra* (Leguminoseae *Allium sativum* {Liliaceae) | Herpes virus type 2 Rauscher murine leukemia virus Cytomegalovirus; herpes simplex 1 virus; |
| | *Aloe vera* {Liliaceae) | herpes simplex 2 virus |
| | *Punica granatum* {Punicaceae) | Cytomegalovirus; herpes simplex 1 virus |
| | *Ribes nigrum* {Saxifragaceae) | Coxsackie B5 virus; hepatitis B virus; herpes |
| | *Camellia sinensis* {Theaceae) | simplex 1 virus;*** herpes simplex 2 virus |
| | *Curcuma longa* {Zingiberaceae) | Encephalitis virus (tick-borne) |
| | *Zingiber officinale* {Zingiberaceae) | Coxsackie A9 virus; influenza virus A; influenza virus A2 (manheim 57); poliovirus I Hepatitis B virus; vesicular stomatitis virus Herpes simplex 1 virus; rhinovirus type 1-B; virus-lpp1; rauscher murine leukemia virus |
| anti-crustacean | *Annona muricata* (Annonaceae) | *Artemia salina* larvae; *Artemia salina**** |
| | *Zingiber officinale* {Zingiberaceae) | *Aremia salina* |
| Insecticide | *Annona muricata* (Annonaceae) | *Macrosiphoniella sanborni**** |
| | *Annona reticulata* {Annonaceae) | *Macrosiphoniella sanborni;*** Oryzaephilus* |
| | *Annona squamosa* (Annonaceae) | *surinamensis; Tribolium castaneum Callosobruchus chinensis; Drosophila* |
| | *Cucurbita pepo* (Cucurbitaceae) | *melanogaster; M. Sanborni;*** Musca* |
| | *Mammea americana* {Guttiferae) | *Domestica; Pediculus Capitis* |
| | *Mentha spicata* (Labiatae) | *Culex quinquefasciatus* |
| | *Ocimum basilicum* (Labiateae) | *Aedes aegypti;*** Serotoma* |
| | *Rosmarinus officinalis* (Labiatae) | *ruficornis*, adults*** |
| | *Citrus reticulata* {Rutaceae) | *Drosophila auraria*; Mites (Pyroglyphidae) |
| | *Curcuma longa* {Zingiberaceae) | *Culex quinquefasciatus Drosophila auraria Sitophilus granarius Macrosiphum euphorbiae* |
| Larvicidal | *Annona squamosa* | *Anopheles stephensi* larvae |
| | *Mammea americana* {Guttiferae) | *Diaphania hyalinata; Laphygma frugiperda**** |
| | *Ocimum Basilicum* (Labiateae) | *Culex fatigans;*** Diacrisia obliqua* |
| | *Allium sativum* {Liliaceae) | *Culex pipiens-quinquefasciatus* (1st instar |
| | *Curcuma longa* {Zingiberaceae) | larvae) *Spodoptera litura* Larvae |
| Molluscicidal | *Annona squamosa* (Annonaceae) | *Biomphalaria straminea* |
| | *Ocimum Basilicum* (Labiateae) | *Biomphalaria pfeifferi* |
| | *Camellia sinensis* {Theaceae) | *Biomphalaria glabrata* |
| Antinematodal | *Glycyrrhiza glabra* (Leguminoseae | *Meloidogyne Incognita**** *Heterodera glycines* |
| | *Phaseolus vulgaris* {Leguminosae) | |

***strong activity for phytochemical

One aspect of the present invention provides coating compositions, especially a marine coating for the antifouling treatment of the submerged portion of the hull of a ship or boat, and most especially for inhibiting the fouling of submerged aquaculture apparatus, including, but not limited to, nets, cages, ropes and the like commonly used in the industry, comprising an environmentally friendly antifouling additive in the form of at least one phytochemical. In general terms, the present invention is directed to polymers containing phytochemicals and methods of making and using the same such as; UHMW polyethylene and VHMW polyethylene coatings and other compression polymers. These polyetheylenes have to be applied using rubber, silicone or acrylic adhesives. Phytochemicals especially useful in the present invention include, but are not limited to, grapefruit seed extract, *capsicum*, capsaicin, polymers containing phytochemicals and methods of making and using the same pomegranate extract of rind, pulp & seed, menthol, camphor, camphor oil, zosteric acid, *Zostera noltil*, partheniol, lemon grass oil, tea tree oil, clove oil, garlic, citric acid, vitamin E, and other phytochemicals exhibiting biocidal activity to be used in any combination. Grapefruit Seed Extract is an effective phytochemical biocide with activity against bacteria, fungi, and some parasites, an example of which is available commercially as P-50 from Chemie Research, Castleberry, Fla. Partheniol, a compound taken from the guayule plant, prevents fouling on wood and metal surfaces. The rate of migration or the release of the phytochemical composition contained within the marine paints, coatings and polymers may be modified by further including in the compositions a release agent such as Vitamin E, a chemical releaser such as citric acid, or an anti-oxidant such as Vitamin E. The chemical releaser may be the same as the phytochemical agent. Vitamin E further possesses antimicrobial properties, and thus may itself function as a biocidal phytochemical, which may work in conjunction with or separately from marine paint binders.

Phytochemicals suitable for use in the compositions of the present invention and which are known to function as antioxidants, as well as to possess antimicrobial properties include, but are not limited to, *Panax ginseng; Panax quinquefolius; Bixa orellana; Humulus lupulus; Spinacia oleracea; Arctium lappa; Cichorium intybus; Cynara scolymus; Helianthus annuus; Inula helenium; Armoracia rusticana; Momordica charantia; Vaccinium corymbosum; Vaccinium myrtillus; Avena sativa; Oryza sativa; Lavandula latifolia; Marrubium vulgare; Melissa officinalis; Mentha pulegium; Mentha spicata; Nepeta cataria; Ocimum basilicum; Origanum onites; Perilla frutescens; Prunella vulgaris; Rosmarinus officinalis; Salvia officinalis; Salvia sclarea; Satureja hortensis; Thymus vulgaris; Laurus nobilis; Arachis hypogaea; Glycine max; Glycyrrhiza glabra; Glycyrrhiza uralensis; Lens culinaris; Phaseolus coccineus; Phaseolus lunatus; Phaseolus vulgaris; Phaseolus vulgaris; Pisum sativum; Psophocarpus tetragonolobus; Pueraria lobata; Tamarindus indica; Tamarindus indica;\* Viciafaba; Vigna angularis; Vigna mungo; Vigna radiata; Allium ampeloprasum; Allium cepa; Allium sativum; Asparagus officinalis; Linum usitatissimum; Morus alba; Eucalyptus globulus; Pimenta dioica; Syzygium aromaticum; Olea europaea; Oenothera biennis; Sesamum indicum; Plantago asiatica; Fagopyrum esculentum; Prunus cerasus; Prunus spinosa; Rosa canina; Rubus fruticosus; Rubus idaeus; Coffea arabica; Citrus aurantium; Citrus paradisi; Ribes nigrum; Ribes rubrum; Capsicum frutescens; Solanum tuberosum; Solanum tuberosum;\* Theobroma cacao; Camellia sinensis; Coriandrum sativum; Cuminum cyminum; Daucus carota; Trachyspermum ammi; Vitis vinifera; Curcuma longa; Zingiber officinale*. Other antioxidants that are useful in the present invention include, but are not limited to, lysine, butylatedhydroxytoulene (BHT), butylatedhydroxyanisole (BHA), grape seed extract, Pine Bark extract (Proanthocyanidins), beta carotene, bilberry extract, ascorbic acid, *Ginkgo biloba* extract, green tea extract, tumeric, zinc picolinate, zinc oxide, iron oxide, calcium carbonate and selenium. Selected antioxidant(s) may be used alone or in combination when combined with the phytochemical(s) in the coating formulas of the present invention.

For applications using leaching paints (coatings), ablative paints (coatings) or self-polishing coatings (polymers) wherein the phytochemical component of the paint compositions comprises the *capsicum*, synthetic capsaicin, tannin, tannic acid, camphor, camphor oil, *Zostera noltil*, and/or menthol for their antimicrobial activity, with or without a migration release agent, the components of the leaching paints (coatings), ablative paints (coatings) and self-polishing polymers (coatings) may contain any combination of the primers, resins, pigments, solvents, paint binders and anti-settling agents known to those of skill in the art that provide effective application properties to, for example, the submerged region of a ship's hull and aquaculture systems.

The amounts of the biocidal agents added to the composition are also dependent upon the particular application. Factors to consider are the conditions under which the composition is to be used, the microorganisms to be inhibited, the duration of the use, whether the object to be protected is a submerged, and the active concentration of the antimicrobial agents that is desired. For example, capsicum can be added in an amount from about 1 ppm to about 2,000,000 ppm, depending upon the desired application.

It should be understood that the present invention is broadly drafted, in one embodiment, towards incorporating phytochemicals as biocidal agents into polymeric materials suitable for the coating of submerged surfaces. In several preferred embodiments of the present invention, *capsicum*, citric acid extract, and grapefruit seed extract may be used as biocidal agents. The present invention, however, encompasses the use of many other biocidal agents. In the various embodiments of the invention, a preferred phytochemical is *capsicum*/synthetic capsaicin alone or in combination with other phytochemicals is used as a fouling preventive agent in marine paints (coatings). *Capsicum* is a food or food seasoning commonly known as "hot pepper." The active heat ingredient in *capsicum* is capsaicin which is a mixture of two unsaturated and three saturated homologs. This mixture is also referred to as capsaicinoids, and includes dihydrocapsaicin and nordihydrocapsaicin. The pungency of capsaicin (capsiacinoids) is measured in Scoville heat units and typically range from 60,000 to 1,500,000 heat units. The compositions of the present invention comprise *capsicum* having Scoville heat units derived from natural *capsicum* or synthetic capsacin from 60,000 to 1,500,00 scoville heat units. The pungency (the heat ingredients) of the *capsicum* may be removed of, either partially or totally, for use as an antifouling additive in marine coatings, even though the heat unit index.

Chemical ingredients in *capsicum* are known to have antimicrobial activity, such as; 1,8-cineole, acetic acid, alpha-terpineol, benzaldehyde, beta-ionone, caffeic acid, caryophyllene, chlorogenenic acid, cinnamic acid, delta-3-carene, ferulic-acid, limonene, myrcene, p-coumaric-acid, pulegone, querectin, rutin, scopoletin, terpinen-4-ol and thujone.

Also useful in the present invention as a fouling preventive additive in marine paints (coatings) is the phytochemical tannic acid. Tannins are classified into two broad groups: the hydrolysable and the condensed or non-hydrolysable tannins. The hydrolysable tannins are usually compounds containing a central core of glucose or other polyhydric alcohol esterified with gallic acid (gallotannins) or hexahydroxydiphenic acid (ellagitannins). The condensed ones are mostly flavolans or polymers of flavan-3-ols (catechins) and/or flavan 3:4-idols (leucoanthocyanidins). They are more resistant to breakdown. Frequently, tannins isolated from a plant bear the characteristics of both groups. Tannins may occur in almost any part of a plant-root, stem, trunk bark, leaves and fruit.

The compositions of the invention further comprise a menthol such as, but not limited to, mentholpropylreneglycolcarbonate. A particularly useful synthetic menthol preparation for inclusion in the compositions of the present invention is FRESCALIN™ (Symrise GmbH & Co, Holzminden, Germany) and comprising at least 50% by weight of isopulegol, between 25% and 49.99% by weight of 5-methyl-2-(1-methylethyl)-cyclohexanol and between 25% and 49.99% by weight of mentholpropylreneglycolcarbonate. This synthetic menthol preparation is especially effective in combination with *capsicum* at inhibiting marine growth when included in anti-fouling paints and coatings.

The compositions of the invention may further comprise extracts from *Renilla reniformis* including the antifoulant diterpenes Renillafoulin A, Renillafoulin B, Renillafoulin C and the like and combinations thereof.

The compositions of the invention further comprise pomegranate, *Punica granatum*, L. (punicaceae) using in whole or in part as fractions the following active chemicals found in pomegranate 1,2,3,4,6-PENTA-O-GALLOYL-BETA-D-GLUCOSE; 1,2,4,6-TETRA-O-GALLOYL-BETA-D-GLUCOSE; ASCORBIC-ACID; ASIATIC-ACID; BETA-SITOSTEROL; BETULINIC-ACID; BORIC-ACID; CALCIUM-OXALATE; CASUARININ; CHLOROGENIC-ACID; CITRIC-ACID; CORILAGIN; DELPHINIDIN-3-GLUCOSIDE; ELAIDIC-ACID; ELLAGIC-ACID; ELLA-GITANNIN; ESTRADIOL; ESTRONE; FRIEDELIN; GALLIC-ACID; GRANATIN-A; GRANATINS; ISOPEL-LETIERINE; LINOLEIC-ACID; MALIC-ACID; MALVI- DIN; MALVIDIN-PENTOSE-GLYCOSIDE; MASLINIC-ACID; NEO-CHLOROGENIC-ACID; NIACIN; PALMITIC-ACID; PANTOTHENIC-ACID; PELLETIERINE; PHOSPHATIDYL-CHOLINE; POLYPHENOLS; PROTOCATECHUIC-ACID; PUNICAFOLIN; PUNICALAGIN; PUNICALIN; RIBOFLAVIN; SORBITOL; STEARIC-ACID; STRICTININ; SULFUR; TANNIN; THIAMIN; URSOLIC-ACID; Pomegranate extract and certain prepared fractions is especially effective in combination with Grapefruit Seed Extract at inhibiting marine growth when included in anti-fouling paints and coatings.

The compositions of the present invention may further include a chemical releaser, which is used to facilitate the controlled release of the phytochemical from the polymer matrix. The chemical releaser facilitates the release of the phytochemical composition from the polymer or paint. The releaser may be, for example, citric acid, a phytochemical that also exhibits antibacterial activity. Zinc oxide, iron oxide or citric acid extract can be added to the polymer or paint (coatings) alone or in combination with other phytochemicals, with or without anti-oxidants like Vitamin E. The release agents used in the phytochemicals and the release agents used in the and polymer coatings can have a synergistic effect, depending on the desired release containing phytochemicals to prevent marine organism fouling.

The amounts (by volume) and combinations (number) of the phytochemical agents added to the coatings may be adjusted according to the particular application, relevant factors including the conditions under which the phytochemical composition is to be used, thickness of the polymer coating, the rate of release of the phytochemical, polishing rate, the types of marine organisms that need controlling may vary, the duration of the use of the phytochemicals in these coatings, and the active concentration of the phytochemical desired. In some cases there may be a need for additional substances such as wetting or emulsifying agents, pH buffering agents, adjuvants, gelling or viscosity enhancing additives, preservatives, colors, and the like, depending upon the use. The present invention also provides biocidal polymer coatings formulated for application in non-marine environments such as architectural polymer coatings. In such cases, the biocidal agents released into the environment will not be as great as when immersed in marine or freshwater conditions.

When making any of the compositions of the present invention, the phytochemicals, antioxidants, and chemical releasers may be added either together or sequentially to the polymer coatings. The mixture is then mixed until the phytochemicals are evenly dispersed within the polymer coatings before processing of the polymer coating. The applications of the finished product may be compression molded, form molded, sprayed, brushed or extruded.

In various embodiments of the polymer coatings of the present invention, biocidal phytochemicals of the present invention may be added in any combination for fouling-release coatings at levels of at least 0.001% to about 60% by weight.

In one embodiment of the present invention, the phytochemicals can be active in the inhibition or control of hard marine fouling (e.g. barnacles) and soft fouling (for example by algae) or a phytochemical may only be active against one type of fouling, and therefore a combination of phytochemicals is required to achieve efficacy.

In various embodiments of the invention, the phytochemical *capsicum*, having a degree of pungency of between 50,000 to 1,500,000 Scoville heat units, is combined with one or more other biocidal phytochemicals and added to a marine paint or coating to control marine fouling.

In other embodiments of the invention, the phytochemical *capsicum*, having a degree of pungency of between 50,000 to 1,500,000 Scoville heat units, is combined with one or more other biocidal phytochemicals and added to an architectural paint or coating to control marine fouling.

In one embodiment, the phytochemical, *capsicum* may be combined with other phytochemicals and added to marine paint to control marine fouling, wherein the *capsicum* is substantially free of the heat causing ingredient capsaicin.

The phytochemical grapefruit seed extract may be added to polymer coatings to control marine fouling. In one embodiment of the invention, the phytochemical grapefruit seed extract may be processed into a concentrated state and the glycol substantially removed from the extract before adding to the polymer coating. In another embodiment, the phytochemical may be selected from extracts of cloves, garlic and/or clove oil.

In preferred embodiments of the invention, the paint may comprise a paint base, grapefruit seed extract, a menthol such as FRESCALIN™ and *capsicum*.

In another embodiment, the phytochemical may include grapefruit seed extract, which exhibits anti-bacterial, anti-parasitic, and anti-fungal activity. Grapefruit seed extract is available commercially as P-50 from Chemie Research, Castleberry, Fla. The grapefruit seed extract can be added to architectural and marine polymer coatings alone or in combination with other phytochemical.

In another embodiment, the phytochemical may include Pomegranate Extract alone, or in combination with Grapefruit Seed Extract. The extract Pomegranate rind, seed and pulp has shown to have algicide properties. Pomegranate Extract in combination with Grapefruit Seed Extract in combination has shown to have a synergist antimicrobial effect.

In an alternative embodiment, the phytochemical camphor is used in combination with other phytochemicals as a marine organism-fouling preventive. Camphor is a crystalline ketone derived from the wood of the camphor tree *Cinnamomum camphora*.

In another alternative embodiment, the paint phytochemical additive for fouling prevention may be lemon grass oil which is a natural by-product of lemon grass and is extracted by steam and other nontoxic extraction methods. Lemon grass oil exhibits anti-fungal and anti-bacterial activity and may be added to marine paints in combination with other phytochemicals. Antioxidants, such as Vitamin E, or releasers, such as citric acid may also be added with the phytochemical composition to the polymer coatings.

In yet another alternative embodiment, the polymer coating-fouling preventive may be Tea Tree Oil. Tea Tree Oil is a natural by-product of the tea tree, (*Melaleuca* species). Tea Tree Oil is extracted through natural non-toxic processes such as steam. Tea Tree Oil exhibits anti-fungal and anti-bacterial activity. Tea Tree Oil may be added to polymer coatings in combination with other phytochemicals, releasers like citric acid, or antioxidants like Vitamin E.

In other embodiments of the compositions of the present invention, the phytochemical component may be selected from tannic acid (tannins), menthol or derivatives thereof, camphor oil, clove and/or clove oil and garlic.

In one embodiment of the compositions of the present invention, the phytochemical combination comprises *capsicum* having between 50,000 and 1,500,000 Scoville units, tannic acid and menthol or a derivative thereof. In another embodiment the phytochemical combination comprises *capsicum* having between 50,000 and 1,500,000 Scoville units, tannic acid, clove oil, garlic and menthol. In yet another embodiment the phytochemical combination comprises *cap-

*sicum* having between 50,000 to 1,500,000 Scoville heat units), tannic acid, garlic and clove oil.

In one embodiment of the paints and coatings of the present invention, the phytochemical combination comprises *capsicum* having between 50,000 to 1,500,000 Scoville heat units and clove oil and optionally garlic. In another embodiment the phytochemical combination comprises *capsicum* having between 50,000 to 1,500,000 Scoville heat units, clove oil, garlic and *Zostera noltil*, with or without vitamin E. In one embodiment the phytochemical combination comprises *capsicum* having between 50,000 to 1,500,000 Scoville heat units), tannic acid, menthol and *Zostera noltil*. In still another embodiment the phytochemical combination comprises *capsicum* having between 50,000 to 1,500,000 Scoville heat units), tannic acid, camphor, pomegranate, menthol and *Zostera noltil*.

In embodiments of the polymer coatings of the present invention, biocidal phytochemicals of the present invention may be added in any combination to polymer coatings, at levels from about 0.1% to about 60% by volume or 0.1% to about 60% lbs/100 lbs of polymer.

In other embodiments of the polymer coatings of the present invention, phytochemicals of the present invention may be added in any combination to levels from about 0.001% to about 40% by volume. or 0.001% to about 40% lbs/100 lbs of polymer In embodiments of the polymer coatings of the present invention, phytochemicals of the present invention may be added in polymer coatings at levels from about 10% to about 60% by volume or 0.1% to about 60% lbs/100 lbs of polymer.

One aspect of the invention, therefore, is a composition comprising a polymer base and a biocidal composition comprising a grapefruit seed extract, a pomegranate extract, a *capsicum* preparation, and a menthol.

One embodiment of this aspect of the invention is a composition wherein the polymer base is selected from a UHMW polyethylene, VHMW polyethylene and a latex-based compound.

In the embodiments of this aspect of the invention, the biocidal composition may comprise one or more biocidal phytochemical agents isolated from a grapefruit seed extract or a pomegranate extract.

This aspect of the invention further encompasses compositions further comprising one or more biocidal phytochemical agents, wherein the biocidal phytochemical agent is an anti-bacterial; an anti-viral; an anti-fungal; an anti-crustacean; a larvicidal; an insecticidal; a molluscicidal or an anti-nematodal biocidal phytochemical.

In the embodiments of the invention, the anti-bacterial biocidal phytochemical may be isolated from *Annona muricata* {Annonaceae), *A. squamosa, Panax ginseng* {Araliaceae), *Capparis spinosa* {Capparidaceae), *Calendula officinalis* {Compositae), *Cynara scolymus* {Compositae), *Cucurbita pepo* {Cucurbitaceae), *Cymbopogon citratus* {Gramineae), *Mentha spicata* {Labiatae), *Ocimum basilicum* {Labiatae), *Rosmarinus officinalis* {Labiatae), *Glycyrrhiza glabra* {Leguminosae), *Allium sativum* (Liliaceae), *Aloe vera* {Liliaceae), *Citrus reticulata* {Rutaceae), *Oenothera biennis* {Onagraceae), *Plantago major* {Plantaginaceae), *Punica granatum* {Punicaceae), *Ribes nigrum* {Saxifragaceae), *Camellia sinensis* {Theaceae), *Curcuma longa* {Zingiberaceae), *Zingiber officinale* {Zingiberaceae) or an alga, the anti-fungal biocidal phytochemical may be isolated from *Annona muricata* {Annonaceae), *Panax ginseng* {Araliaceae), *Capparis spinosa* (Capparidaceae), *Calendula officinalis* (Compositae), *Cucurbita pepo* (Cucurbitaceae), *Cymbopogon citratus* (Granimeae), *Mentha spicata* (Labiatae), *Ocimum basilicum* (Labiatae), *Rosmarinus officinalis* (Labiatae), *Glycyrrhiza glabra* (Leguminoseae), *Allium sativum* (Liliaceae), *Aloe vera* (Liliaceae), *Sesamum indicum* {Pedaliaceae), *Punica granatum* {Punicaceae), *Citrus aurantium* {Rutaceae), *Citrus reticulata* {Rutaceae), *Ribes nigrum* {Saxifragaceae), *Camellia sinensis* {Theaceae), *Curcuma longa* {Zingiberaceae) or *Zingiber officinale* {Zingiberaceae) or an alga, the anti-crustacean biocidal phytochemical may be isolated from *Annona muricata* (Annonaceae) or *Zingiber officinale* {Zingiberaceae), the larvicidal biocidal phytochemical is isolated from *Annona squamosa, Mammea americana* {Guttiferae), *Ocimum Basilicum* (Labiateae), *Allium sativum* {Liliaceae) or *Curcuma longa* {Zingiberaceae), the insecticidal biocidal phytochemical may be isolated from *Annona muricata* (Annonaceae), *Annona reticulata* {Annonaceae), *Annona squamosa* (Annonaceae), *Cucurbita pepo* (Cucurbitaceae), *Mammea americana* {Guttiferae), *Mentha spicata* (Labiatae), *Ocimum basilicum* (Labiateae), *Rosmarinus officinalis* (Labiatae), *Citrus reticulata* {Rutaceae) or *Curcuma longa* {Zingiberaceae), the molluscicidal biocidal phytochemical may be isolated from *Annona squamosa* (Annonaceae), *Ocimum Basilicum* (Labiateae) or *Camellia sinensis* {Theaceae) and the anti-nematodal biocidal phytochemical may be isolated from *Glycyrrhiza glabra* (Leguminoseae) or *Phaseolus vulgaris* {Leguminosae).

Another aspect of the invention is a coating composition comprising a polymer base selected from UHMW polyethylene, VHMW polyethylene, a latex compound or a vinyl acrylic, and an environmentally friendly antifouling biocidal composition comprising a grapefruit seed extract, a pomegranate extract, a *capsicum* preparation and a menthol, and optionally an additive in the form of one or more biocidal phytochemical agents.

In various embodiments of this aspect of the invention, the coating composition is a marine coating for suitable for application to a submerged surface or the submerged portion of an aquaculture system.

In one embodiment of the invention, the composition comprises a marine coating further comprising a rubber, silicone or acrylic adhesive.

In other embodiments according to the invention, the composition further optionally comprises one or more biocidal phytochemical agents is selected from a camphor, a camphor oil, zosteric acid, *Zostera noltil*, partheniol, a lemon grass oil, a tea tree oil, a tannic acid, a tannin, a clove oil and a garlic, or a isolated component thereof.

Other embodiments of the compositions according to the present invention further comprise at least one additive selected from the group consisting of a leaching paint, a ablative paints or a self-polishing coating, wherein the components of the additive comprise one or more of a primer, a resin, a pigment, a solvent, a paint binder and an anti-settling agent.

Still other embodiments of the invention further comprise a chemical releaser, wherein the chemical releaser facilitates a controlled release of a biocidal phytochemical from the polymer.

In one embodiment of the invention, the chemical releaser is selected from citric acid, zinc oxide, iron oxide, vitamin E.

Yet other embodiments of the compositions of the invention may further comprise one or more additives selected from the group consisting of a wetting or emulsifying agent, a pH buffering agent, a gelling or viscosity enhancing agent, a preservative and a coloring agent.

In the embodiments of the invention, the *capsicum* preparation is about 1 ppm to about 2,000,000 ppm. and the menthol is mentholpropylreneglycolcarbonate or a synthetic derivative thereof.

In other embodiments of the invention, the compositions may further comprise an extract from *Renilla reniformis*, wherein the extract comprises a diterpene, Renillafoulin A, Renillafoulin B, Renillafoulin C, or any combination thereof.

Yet another aspect of the invention is a method of inhibiting the fouling of a submerged surface or the submerged portion of an aquaculture system comprising applying to a surface or an aquaculture system to be submerged an antifouling coating comprising a composition according to the present invention.

In embodiments of this aspect of the invention, the antifouling coating can be attached to the submerged or submersible surface or an aquaculture system by an adhesive.

Another aspect of the present invention provides paints, coatings and polymers containing microencapsulated phytochemicals and methods of making and using the same.

Representative groups of coating materials advantageously useful in the present invention to produce microcapsules include, but are not limited to, gums such as gum arabic, agar, sodium alginate, a carageenan; carbohydrates such as starch, dextran, sucrose, corn syrup; celluloses including, but not limited to, carboxymethylcellulose, methycellulose, ethylcellulose, nitrocellulose, acetylcellulose, cellulose acetate-phthalate, cellulose acetate-butylate-phthalate; lipid wax such as paraffin, tristearin, stearic acid, monoglycerides, diglycerides, beeswax, oils, fats, hardened oils; proteins such as, for example, gluten, casein, gelatin, or albumin.

The encapsulation agent will have certain desirable characteristics, depending on the chemical characteristics of the core material, the intended use of the core material, the conditions under which the product will be stored, and the processing conditions to which it will be exposed. Some general characteristics of the encapsulating agent are that it is insoluble in and non-reactive with the core material, have solubility in the end-product and be able to withstand high temperatures of the spray-drying process. Some typical encapsulation agents are dextrans, gums, starches or proteins.

There are many methods to encapsulate compositions, and selection of a method depends on the properties of the core and coating materials. Spray drying is the most frequently used encapsulation method, and is the least expensive. The entrapped ingredient may be, but is not limited to, a fat, oil, or flavor compound, and the coating is usually a carbohydrate. An emulsion is formed between the core and coating, and the emulsion is dried in a hot air drying chamber. This process allows the coating material to trap the core material. Some water-soluble materials can also be encapsulated. This process is slightly different from encapsulating oils, because there is not a clear definition between the core and the coating material, but more of an emulsion of the two phases. Various encapsulation methods suitable for use in the present invention are described in Dziezak, 1988; Jackson and Lee, 1991, incorporated herein in their entireties.

The preparation of a microencapsulated product involves several steps. First, the need for microencapsulation, whether it is to enhance the quality of an existing product or to develop an entirely new product, must be identified. Next, a shell material that provides the desired release characteristics must be chosen. Finally, a process to prepare the microcapsules must be selected.

The microencapsulation process may occur in a spray dryer, and the process involves three steps as described by Dziezak, (1988) incorporated herein by reference in its entirety: first, preparation of the emulsion or dispersion to be processed; second, homogenization of the dispersion; and the last step is atomization of the mass in the drying chamber. Dispersing the active material into the coating material, which is immiscible, makes the dispersion. An emulsifier is then added to the dispersion and the dispersion is then heated and homogenized. This homogenization creates an oil-in-water type of an emulsion. The emulsion is then atomized into a heated air stream supplied to the drying chamber. These atomized particles assume a spherical shape as they fall through the gaseous medium, and the oil is encased in the aqueous phase. The rapid removal of water from the coating material by the cyclone keeps the core material below 100° C.

During the emulsion stage, a 4:1 wall-to-core ratio in the emulsion may be used with volatiles for spray drying, due to a decrease in volatile retention with higher volatile levels (Reineccius, 1988). The moisture content of the coating material may vary with different types of coating materials. For example, 30% solids (w/w) using gum arabic as the coating material is possible (Rosenberg et al. (1990)).

Leaflash (Leaflash-100) may be used to encapsulate compounds unstable to heat such as citral and linalyl acetate (Bhandari et al. (1992). Phytochemical compositions according to the present invention may be encapsulated using gum arabic as the coating. In this experiment the spray dryer had a pressure of $1.4 \times 10^5$ Pa and a flow rate of 70 kg/hr. The drying chamber and feed nozzle were kept at 70° C. The air inlet ranged from 300-400° C. and the air outlet 100-110° C. Under these conditions, the microencapsulated product appeared at the cyclone five seconds after the product (emulsion) feed had begun (Bhandari et al., 1992

There are four typical mechanisms by which the core material is released from a microcapsule: mechanical rupture of the capsule wall, dissolution of the wall, melting of the wall, and diffusion through the wall. Less commonly used release mechanisms, but of particular interest in the application of the present invention is ablation (slow erosion of the shell) or progressive biodegradation.

Complex coacervation may be used to make microcapsules, whereby the substance to be encapsulated is first dispersed as tiny droplets in an aqueous solution of a polymer such as gelatin. For this emulsification process to be successful, the core material should be immiscible in the aqueous phase. Miscibility is assessed using physical chemistry and thermodynamics. The emulsification is typically achieved by mechanical agitation, and the size distribution of the droplets is governed by fluid dynamics.

A second water soluble polymer, such as gum arabic, may then be added to this emulsion. After mixing, dilute acetic acid is added to adjust the pH. Though both polymers are soluble in water, addition of the acetic acid results in the spontaneous formation of two incompatible liquid phases. One phase, called the coacervate, has relatively high concentrations of the two polymers; the other phase, called the supernatant, has low polymer concentrations. The concentrations of the polymers in these two phases, and the pH at which phase separation occurs, are governed by specific properties of physical chemistry, thermodynamics, and polymer chemistry.

The coacervate can preferentially adsorbs onto the surface of the dispersed core droplets, forming microcapsules. Again, physical chemistry and thermodynamics dictate whether the coacervate adsorbs onto the core material. The capsule shells are usually hardened first by cooling (heat transfer), and then by chemical reaction through the addition of a cross-linking agent such as formaldehyde (polymer chemistry). The release characteristics of the microcapsules are governed by materials science (mechanical), heat transport (thermal release), and mass diffusion (diffusion through the wall).

Each aspect of this process may be highly dependent upon the others. For example, the thermodynamics of the phase separation affects the composition of the shell material, and this affects the ability of the shell to wet the core phase, as well as determining the barrier properties and release characteristics.

The following microencapsulated phytochemicals may be used alone or in combination as biocidal compositions in architectural paints, marine paints and coatings, or coatings for aquaculture systems: grapefruit seed extract in an amount from about 5% to about 40% w/v, pomegranate extract in an amount from about 5% to about 40% w/v, menthol in an amount from about 5% to about 40% w/v, zosteric acid, (*Zostera noltil*), in amounts from about 5% to about 40% w/v, and *capsicum*, in an amount from about 0.05% to about 30% w/v. It is contemplated that the phytochemicals may be mixtures of compounds as extracted from the plant source material, or one or more of the biocidal agents isolated from the extract of the active ingredients and used in various combinations. It is further contemplated that in marine paint formulations, cuprous oxide in amounts from about 0.05% to about 25% w/v may be included increase the overall biocidal activity of the paint.

The microencapsulation membrane may comprise any material well-known to one of skill in the art including, but not limited to, gums such as, for example, gum arabic, agar, sodium alginate, a carageenan; carbohydrates such as starch, dextran, sucrose, corn syrup; celluloses including, but not limited to, carboxymethylcellulose, methycellulose, ethylcellulose, nitrocellulose, acetylcellulose, cellulose acetate-phthalate, cellulose acetate-butylate-phthalate; lipid wax such as paraffin, tristearin, stearic acid, monoglycerides, diglycerides, beeswax, oils, fats, hardened oils; proteins such as, for example, gluten, casein, gelatin, or albumin.

The present invention, therefore, provides durable polymeric liquid (such as paints) or solid (such as a polymeric coating of a catheter or food wrapping, comprising a paint or polymeric base and at least one biocidal phytochemical agent, wherein the biocidal agent is microencapsulated. Microencapsulation of the biocidal agent(s) allows for a sustained release of the agent thereby increasing the effective life of the applied paint or coating and may serve to protect the agent(s) from the paint or polymer base during manufacture or application. Release of the agent from the microcapsules will be by several possible means including mechanical rupture, ablation, thermal release, permeation, dissolution, delayed and targeted release, pH and osmotic release, photolytic release, biodegradation, or triggered release. By microencapsulating the biocidal phytochemicals before addition to the paint or polymer base, protection may be afforded to the phytochemicals that may otherwise interact with the components of the paint or polymer base and thereby lose their effectiveness. Furthermore, microencapsulation may allow the paint or polymer compositions to comprise a greater proportion of the phytochemical without reducing the mechanical or other desirable properties of the paint or polymer medium that may otherwise occur if the phytochemicals were added directly to the paint or polymer base. Accordingly, the present application provides a paint or polymer comprising a microcapsule component, wherein the microcapsules comprise at least one biocidal phytochemical and a capsule coat. The microcapsules may constitute from about 0.05% w/v to about 90% w/v of the final paint or polymer. In one embodiment, the microcapsules may constitute from about 0.05% w/v to about 75% w/v of the final paint or polymer. In another embodiment, the microcapsules may constitute from about 5% w/v to about 75% w/v of the final paint or polymer. In another embodiment, the microcapsules may constitute from about 20% w/v to about 75% w/v of the final paint or polymer. In yet another embodiment, the microcapsules may constitute from about 50% w/v to about 75% w/v of the final paint or polymer. In another embodiment, the microcapsules may constitute from about 0.05% w/v to about 50% w/v of the final paint or polymer. In still another embodiment, the microcapsules may constitute from about 0.05% w/v to about 25% w/v of the final paint or polymer. In another embodiment, the microcapsules may constitute from about 0.05% w/v to about 10% w/v of the final paint or polymer.

The following microencapsulated phytochemicals may be used alone or in combination and as biocidal compositions for wood treatment coatings & processes: cashew nut shell liquid (CNSL) from *Anacardium occidentale*, in amounts from 1% to 50%, marigold root extract in amounts from 1% to 50% w/v, clove oil in amounts from 1% to 50% w/v, garlic (deodorized) in amounts from 1% to 50% w/v, tobacco dust extract, in amounts from 1% to 50%, *capsicum* (other alkaloids), Capsaicin (synthetic), both in amounts from 0.05% to 30%, guayule plant extract (partheniol), in amounts from 1% to 50% w/v, grapefruit seed extract, in amounts from 1% to 50% w/v, pomegranate extract, in amounts from 1% to 50% w/v, tannic acid, in amounts from 1% to 50% w/v, menthol (or lactones) in amounts from 1% to 50% w/v, zosteric acid, (*Zostera noltil*), in amounts from 5% to 40% w/v, and neem oil, in amounts from 1% to 50% v/v.

The following microencapsulated phytochemicals may be advantageously used alone or in combination and as biocidal compositions for filter membranes: crude cashew nut shell liquid (CNSL) comprises non-isoprenoid phenolic lipids such as anacardic acids, cardols, cardanols, methylcardols, and wood materials. CNSL has found important commercial usage as a phenolic raw material for the manufacture of certain resins and plastics.

The following microencapsulated phytochemicals may advantageously be used alone or in combination as biocidal compositions for inclusion in polymeric film coatings of urinary indwelling catheters; grapefruit seed extract in an amount from about 5% w/v to about 40% w/v, and pomegranate extract, in an amount from about 5% w/v to about 40% w/v.

The amounts of the phytochemical biocidal agents added to the compositions may be varied depending upon the particular application. Factors to consider are the conditions under which the composition is to be used, the microorganism(s) to be inhibited, the duration of the use. The intended use of the microencapsulated phytochemicals will also direct the selection of the paint or polymer base. For example, a surface submerged will require that the paint or coating is water resistant, whereas a coating for a catheter will require that the polymer base is non-toxic to the recipient patient.

When making any of the compositions of the present invention, the phytochemicals, antioxidants, and chemical releasers may be added either together or sequentially to marine paints, coatings and polymers. The mixture is then mixed until the phytochemicals are evenly dispersed within the paint, coating or polymer. The applications of the finished product may be brushed or sprayed on a surface to be coated.

Microencapsulation of the biocidal phytochemical agents and inclusion in wood treatment compositions would ensure long term efficacy of wood treatment thereby extending the useful life of the phytochemicals from months to years due to microencapsulation. There are several forms of wood treatment. Coatings that are soaked, sprayed or brushed on to wood surfaces and pressure treatment methods that permeate the wood matrix, as examples. Pressure treated wood is used in many structures. For example, houses, commercial buildings, decks, fences, retaining walls, picnic tables, fiber board, plywood, docks, boathouses, marine pilings, bulkheads, dune crossovers, boardwalks, pole homes and other places where the wood is exposed to rot, insect attack or other forms of biodeterioration. The basic treating process is a simple and highly controlled preservative mixture of a stable phytochemical formula microencapsulated and used in wood treatment and coatings to form insoluble precipitates. The microencapsulation of the biocidal phytochemical agents would insure long term efficacy of wood treatment thereby extending the useful life of the phytochemicals from months to years due to microencapsulation. The compositions of the present invention may further include a specific triggering release a mechanism of the encapsulated phytochemicals. The encapsulation trigger mechanism facilitates the release of the phytochemical composition from the wood or wood composite. The microencapsulation release mechanism may be, for example, Mechanical rupture, Thermal release, Permeation, Dissolution, Delayed and targeted release, pH and osmotic release, Photolytic release, Biodegradation or Triggered release.

The present invention provides coating compositions comprising environmentally benign phytochemicals suitable for use in preventing decay and destruction of wood and wood products by bacteria, algae, molds or fungal organisms and pests such as termites, rodents and worms by using a combination of phytochemicals proven to control unwanted organisms and pests. For example, the following phytochemicals may be microencapsulated in different combinations for wood treatment and wood coating formulas:

Cashew nut shell liquid (CNSL) from *Anacardium occidentale*, Crude cashew nut shell Cashew nut shell (liquid) extract, Marigold Root extract, Clove oil, Garlic (deodorized), Tobacco Dust extract, *Capsicum* (other alkaloids), Capsaicin (synthetic), Guayule plant extract (Partheniol), Grapefruit Seed Extract, Pomegranate Extract, Tannic Acid, Zosteric Acid, *Zostera noltil*, Menthol (and other Lactones) and Neem oil. Crude cashew nut shell liquid is a naturally occurring non-isoprenoid phenolic lipids such as anacardic acids (1) cardols (2) cardanols (3) methylcardols (4) and wood materials. CNSL has found important commercial usage as a phenolic raw material for the manufacture of certain resins and plastics. CNSL in synthesized as macrolide lasiodiplodin.

Microencapsulation of biocidal phytochemical agents used in various types of filter membranes may extend the useful life of the phytochemicals from months to years. Filters in general are collection systems of unwanted materials contained in liquids or air as liquids or air passes through the filtration system. Membrane filtration types for which the compositions of the present invention are suitable may be used for such as gas separation, pervaporation, microfiltration, UF, NF, reverse osmosis, capture and hold materials that often contain pathogens or fouling organisms that can replicate and grow in or on the filter membrane causing the filters to become less productive and thereby increasing cost and decreasing overall efficiency. The microencapsulation of the biocidal phytochemical agents will increase long term efficacy of filter membranes, thereby extending the useful life of the phytochemicals from months to years due to microencapsulation. The encapsulation trigger mechanism facilitates the release of the phytochemical composition from the filter membrane. The microencapsulation release mechanism may be, for example, mechanical rupture, thermal release, permeation, dissolution, delayed and targeted release, pH and osmotic release, photolytic release, biodegradation or triggered release.

The present invention also encompasses polymer films comprising microencapsulated phytochemicals that may be used to coat any fibrous material to prevent or inhibit the growth of organisms thereon. For example, glass fiber may be pre-treated with a latex or other polymer coating that includes microencapsulated phytochemicals such as menthol, grape fruit seed extract, or pomegranate extract, or isolated components thereof, or any combination such as menthol, grape fruit seed extract and pomegranate extract, with biocidal activity. The treated glass-fiber may then be used to form filters. The biocidal coatings thereof according to the present invention will be able to prevent the growth of microorganisms, fungi and the like that may colonize the filter material during storage or use, especially under high humidity conditions.

The present invention further encompasses the microencapsulation of the biocidal phytochemical agents and their incorporation into a polymer coating, e.g., a latex coating, that insure long term efficacy of implanted medical devices such as an indwelling urinary catheters. Currently, there is a need for the coating of indwelling urinary catheters with antimicrobial agents other than silver oxide, for example. The microencapsulation of biodical phytochemicals in the latex or non-latex matrix of catheters would ensure the time release of active ingredients and also enhance the shelf-life of the catheters containing the biodical phytochemical agents. The encapsulation trigger mechanism facilitates the release of the phytochemical composition from catheter's latex matrix. The microencapsulation release mechanism may be, for example, thermal release, dissolution, delayed and targeted release, pH and osmotic release. The selection of the antimicrobial phytochemicals for incorporation into this aspect of the invention depends not only on their having antimicrobial activity, but also being physiologically and pharmaceutically acceptable to a recipient patient. For example, a combination of menthol and pomegranate extract would be acceptable, inclusion of *capsicum* without microencapsulation would result in significant irritation of the patients' tissues.

In another embodiment, the phytochemical may include pomegranate extract prepared from the rind, seed, pulp, leaf or bark or a combination of any of those plant parts used alone or in combination with any other phytochemical.

In another embodiment, the phytochemical may include pomegranate extract and grapefruit seed extract, which when combined, have shown to control a wide range of soft fouling, such as, brown and green algae, as an example.

In another embodiment, the phytochemical may include various fractions of the active ingredients of pomegranate extract and grapefruit seed extract combined with menthol and *capsicum*.

It should be understood that the present invention is not limited to the specific compositions or methods described herein and that any composition having a formula or method steps equivalent to those described falls within the scope of the present invention. Preparation routes of the composition and method steps for treating marine polymer coating surfaces are merely exemplary so as to enable one of ordinary skill in the art to make the composition and use it according to the described process and its equivalents. It will also be understood that although the form of the invention shown and described herein constitutes preferred embodiments of the invention, it is not intended to illustrate all possible forms of the invention. The words used are words of description rather than of limitation. Various changes and variations may be made to the present invention without departing from the spirit and scope of the invention.

The invention will now be further described by way of the following non-limiting example.

Example 1

TABLE 3

Polymer Base No. 1-(No water; No Acrysol)

| COMPONENT | Dry Weight (gm) | Percent Dry Weight[a] (gm/100 gm solid) | Wet weight (gm) | Percent Wet Weight[b] (gm/100 gm solution) |
|---|---|---|---|---|
| CoatOsil 1211 | 0.80 | 4.3 | 0.80 | 2.2 |
| Silwet L-77 | 0.30 | 1.6 | 0.30 | 0.85 |
| Novacryl DP-126 (60.3% solid) | 3.10 | 16.6 | 5.13 | 14.6 |
| Acrygen 8662 (45% solid) | 12.38 | 66.5 | 27.52 | 85.6 |
| Ancamine K-54 | 0.34 | 1.8 | 0.34 | 0.97 |
| CoatOsil 1770 | 1.05 | 5.6 | 1.05 | 3.0 |
| TOTAL | 17.97 | | 38.76 | |

[a]Percent Dry Weight calculated before adding water
[b]Percent Wet Weight calculated after adding water Example 2

TABLE 4

Polymer Base No. 2-(Water; No Acrysol)

| COMPONENT | Dry Weight (gm) | Percent Dry Weight[a] (gm/100 gm solid) | Wet weight (gm) | Percent Wet Weight[b] (gm/100 gm solution) |
|---|---|---|---|---|
| Deionized Water | | | 95.18 | 73.00 |
| CoatOsil 1211 | 0.80 | 4.3 | 0.80 | 0.61 |
| Silwet L-77 | 0.30 | 1.6 | 0.30 | 0.23 |
| Novacryl DP-126 (60.3% solid) | 3.10 | 16.6 | 5.13 | 3.94 |
| Acrygen 8662 (45% solid) | 12.38 | 66.5 | 27.52 | 21.12 |
| Ancamine K-54 | 0.34 | 1.8 | 0.34 | 0.26 |
| CoatOsil 1770 | 1.05 | 5.6 | 1.05 | 0.81 |
| TOTAL | 17.97 | | 130.32 | |

Example 3

TABLE 5

Polymer Base No. 3-(No Water; Acrysol)

| COMPONENT | Dry Weight (gm) | Percent Dry Weight[a] (gm/100 gm solid) | Wet weight (gm) | Percent Wet Weight[b] (gm/100 gm solution) |
|---|---|---|---|---|
| Acrysol RM-825 (28% soild) | 0.74 | 3.11 | 2.64 | 7.0 |
| CoatOsil 1211 | 0.80 | 2.69 | 0.80 | 2.11 |
| Silwet L-77 | 0.30 | 1.26 | 0.30 | 0.8 |
| Novacryl DP-126 (60.3% solid) | 3.10 | 13.05 | 5.13 | 13.6 |
| Acrygen 8662 | 12.38 | 52.11 | 27.52 | 72.84 |
| Ancamine K-54 | 0.34 | 1.43 | 0.34 | 0.9 |
| CoatOsil 1770 | 1.05 | 4.42 | 1.05 | 2.78 |
| TOTAL | 18.63 | | 37.78 | |

The thickness protective colloid (Acrysol RM-825) is added for increased stability and longer shelf life of the liquid mixture. RM-825 is a polyurethane based thickener.

Example 4

TABLE 6

Polymer Base No. 4-(Water; Acrysol)

| COMPONENT | Dry Weight (gm) | Percent Dry Weight[a] (gm/100 gm solid) | Wet weight (gm) | Percent Wet Weight[b] (gm/100 gm solution) |
|---|---|---|---|---|
| Deionized Water | | | 95.18 | 71.59 |
| Acrysol RM-825 | 0.74 | 3.11 | 2.64 | 1.99 |
| CoatOsil 1211 | 0.80 | 2.69 | 0.80 | 0.6 |
| Silwet L-77 | 0.30 | 1.26 | 0.30 | 0.23 |
| Novacryl DP-126 (60.3% wet weight) | 3.10 | 13.05 | 5.13 | 3.86 |
| Acrygen 8662 | 12.38 | 52.11 | 27.52 | 20.7 |
| Ancamine K-54 | 0.34 | 1.43 | 0.34 | 0.26 |
| CoatOsil 1770 | 1.05 | 4.42 | 1.05 | 0.79 |
| TOTAL | 18.63 | | 132.96 | |

Example 5

TABLE 7

Polymer Base No. 5-(No water; Acrysol; Diethyleneglycolbutylether)

| COMPONENT | Dry Weight (gm) | Percent Dry Weight[a] (gm/100 gm solid) | Wet weight (gm) | Percent Wet Weight[b] (gm/100 gm solution) |
|---|---|---|---|---|
| Acrysol RM-825 | 0.74 | 3.11 | 2.64 | 6.18 |
| CoatOsil 1211 | 0.80 | 2.69 | 0.80 | 1.87 |
| Silwet L-77 | 0.30 | 1.26 | 0.30 | 0.7 |
| Novacryl DP-126 (60.3% wet weight) | 3.10 | 13.05 | 5.13 | 12.01 |
| Acrygen 8662 | 12.38 | 52.11 | 27.52 | 64.42 |
| Ancamine K-54 | 0.34 | 1.43 | 0.34 | 0.8 |
| CoatOsil 1770 | 1.05 | 4.42 | 1.05 | 2.46 |
| Diethyleneglycol-butylether | 5.00 | 21.05 | 5.00 | 11.7 |
| TOTAL | 23.71 | | 42.78 | |

Example 6

TABLE 8

Polymer base No. 6-(Water; Acrysol; Diethyleneglycolbutylether)

| COMPONENT | Dry Weight (gm) | Percent Dry Weight[a] (gm/100 gm solid) | Wet weight (gm) | Percent Wet Weight[b] (gm/100 gm solution) |
|---|---|---|---|---|
| Deionized Water | | | 95.18 | 69.0 |
| Acrysol RM-825 | 0.74 | 3.11 | 2.64 | 1.91 |
| CoatOsil 1211 | 0.80 | 2.69 | 0.80 | 0.58 |
| Silwet L-77 | 0.30 | 1.26 | 0.30 | 0.22 |
| Novacryl DP-126 (60.3% wet weight) | 3.10 | 13.05 | 5.13 | 3.72 |
| Acrygen 8662 | 12.38 | 52.11 | 27.52 | 19.96 |
| Ancamine K-54 | 0.34 | 1.43 | 0.34 | 0.25 |
| CoatOsil 1770 | 1.05 | 4.42 | 1.05 | 0.76 |
| Diethyleneglycol-butylether | 5.00 | 21.05 | 5.00 | 3.63 |
| TOTAL | 23.71 | | 137.9 | |

Example 7

TABLE 9

Antifouling Base Composition

| COMPONENT | Dry Weight (gm) | Wet weight (gm) | Percent Wet Weight[b] (gm/100 gm solution) | FUNCTION |
|---|---|---|---|---|
| Menthol** | 1.93 | 1.93 | 12.2 | Antifouling agent |
| Capsicum (20% of wet weight)** | 2.38 | 11.90 | 75.5 | Antifouling agent |
| Tea Tree Oil** | 1.96 | 1.9 | 12.4 | Antifouling agent |
| TOTAL | 9.96 | 15.79 | | |

Example 8

TABLE 10

Antifouling Composition No. 1

| Ingredient | Weight (gm) | Weight Percent |
|---|---|---|
| Pomegranate/Grapefruit Seed Extract* | 625 | 81.86 |
| Bromelain | 91.5 | 11.98 |
| Trypsin | 45.75 | 6.00 |
| Vitamin E | 1.25 | 0.16 |
| Totals: | 763.5 | 100.0% |

*Pomegranate Extract/Grapefruit Seed Extract Composition
Combined Pomegranate Extract, 90% v/v in propylene glycol; Grapefruit Seed Extract, 10% v/v in glycerin
(Diterpene amount = 1.0854 gm/100 ml; Phenolics amount = 0.62 gm/100 ml)

Example 9

TABLE 11

Antifouling Composition No. 2

| COMPONENT | Dry Weight (gm) | Percent Dry Weight[a] (gm/100 gm solid) | Wet weight (gm) | Percent Wet Weight[b] (gm/100 gm solution) |
|---|---|---|---|---|
| Formula No. 1* | 3.69 | 37.1 | 3.69 | 18.94 |
| Menthol** | 1.93 | 19.4 | 1.93 | 9.91 |
| Capsicum (20% of wet weight)** | 2.38 | 23.9 | 11.90 | 61.1 |
| Tea Tree Oil** | 1.96 | 19.7 | 1.96 | 10.1 |
| TOTAL | 9.96 | | 19.48 | |

**The Menthol, Capsicum and Tea Tree Oil must be melted together before mixing with Formula No. 1.
Total polymer solids does not include optional diethyleneglcolbutylether
All ingredients are pre-weighed and added to mixture with agitation thereby avoiding air entrapment.

Example 10

Antifouling of Marine Immersed Painted Surfaces

A biocidal paint was used to coat the surface of a metal plate. Control plates were similarly coated with a paint not containing the biocidal agents, or with a commercially available marine antifouling paint. The plates were immersed in open ocean water and periodically examined for the extent of marine colonization.

At the end of six moths of immersion, the control metal plates were heavily encrusted with both animal and plant growth including brown and green algae, acorn barnacles and marine worms. In contrast, however, the plates treated with the paint had very little marine growth over more than 90% of the exposed surface, and where there was growth it was significantly less than would be expected for the period of exposure used.

It should be understood that the present invention is not limited to the specific compositions or methods described herein and that any composition having a formula or method steps equivalent to those described falls within the scope of the present invention. Preparation routes of the composition and method steps for treating marine surfaces are merely exemplary so as to enable one of ordinary skill in the art to make the composition and use it according to the described process and its equivalents. It will also be understood that although the form of the invention shown and described herein constitutes preferred embodiments of the invention, it is not intended to illustrate all possible forms of the invention. The words used are words of description rather than of limitation. Various changes and variations may be made to the present invention without departing from the spirit and scope of the invention.

The invention is further described by the following numbered paragraphs:

1. A composition comprising a polymer base and a biocidal composition comprising a grapefruit seed extract, a pomegranate extract, a *capsicum* preparation and a menthol.

2. The composition of Paragraph 1 wherein the polymer base is selected from a UHMW polyethylene, VHMW polyethylene and a latex-based compound.

3. The composition of Paragraph 1 wherein the biocidal composition comprises one or more biocidal phytochemical agents isolated from a grapefruit seed extract or a pomegranate extract.

4. The composition of Paragraph 1 further comprising one or more biocidal phytochemical agents, wherein the biocidal phytochemical agent is an anti-bacterial; an anti-viral; an anti-fungal; an anti-crustacean; a larvicidal; an insecticidal; a molluscicidal or an anti-nematodal biocidal phytochemical.

5. The composition of Paragraph 4 wherein the anti-bacterial biocidal phytochemical is isolated from *Annona muricata* {Annonaceae), *A. squamosa, Panax ginseng* {Araliaceae), *Capparis spinosa* {Capparidaceae), *Calendula officinalis* {Compositae), *Cynara scolymus* {Compositae), *Cucurbita pepo* {Cucurbitaceae), *Cymbopogon citratus* {Gramineae), *Mentha spicata* {Labiatae), *Ocimum basilicum* {Labiatae), *Rosmarinus officinalis* {Labiatae), *Glycyrrhiza glabra* {Leguminosae), *Allium sativum* (Liliaceae), *Aloe vera* {Liliaceae), *Citrus reticulata* {Rutaceae), *Oenothera biennis* {Onagraceae), *Plantago major* {Plantaginaceae), *Punica granatum* {Punicaceae), *Ribes nigrum* {Saxifragaceae), *Camellia sinensis* {Theaceae), *Curcuma longa* {Zingiberaceae), *Zingiber officinale* {Zingiberaceae) or an alga, the anti-fungal biocidal phytochemical is isolated from *Annona muricata* {Annonaceae), *Panax ginseng* {Araliaceae), *Capparis spinosa* (Capparidaceae), *Calendula officinalis* (Compositae), *Cucurbita pepo* (Cucurbitaceae), *Cymbopogon citratus* (Granimeae), *Mentha spicata* (Labiatae), *Ocimum basilicum* (Labiatae), *Rosmarinus officinalis* (Labiatae), *Glycyrrhiza glabra* (Leguminoseae), *Allium sativum* (Liliaceae), *Aloe vera* (Liliaceae), *Sesamum indicum* {Pedaliaceae), *Punica granatum* {Punicaceae), *Citrus aurantium* {Rutaceae), *Citrus reticulata* {Rutaceae), *Ribes nigrum* {Saxifragaceae), *Camellia sinensis* {Theaceae), *Curcuma longa* {Zingiberaceae) or *Zingiber officinale* {Zingiberaceae) or an alga, the anti-crustacean biocidal phytochemical is isolated from *Annona muricata* (Annonaceae) or *Zingiber officinale* {Zingiberaceae), the larvicidal biocidal phytochemical is isolated from *Annona squamosa, Mammea americana* {Guttiferae), *Ocimum Basilicum* (Labiateae), *Allium sativum* {Liliaceae) or *Curcuma longa* {Zingiberaceae), the insecticidal biocidal phytochemical is isolated from *Annona muricata* (Annonaceae), *Annona reticulata* {Annonaceae), *Annona squamosa* (Annonaceae), *Cucurbita pepo* (Cucurbitaceae), *Mammea americana* {Guttiferae), *Mentha spicata* (Labiatae), *Ocimum basilicum* (Labiateae), *Rosmarinus officinalis* (Labiatae), *Citrus reticulata* {Rutaceae) or *Curcuma longa* {Zingiberaceae), the molluscicidal biocidal phytochemical is isolated from *Annona squamosa* (Annonaceae), *Ocimum Basilicum* (Labiateae) or *Camellia sinensis* {Theaceae) and the anti-nematodal biocidal phytochemical is isolated from *Glycyrrhiza glabra* (Leguminoseae) or *Phaseolus vulgaris* {Leguminosae).

6. A coating composition comprising a polymer base selected from UHMW polyethylene, VHMW polyethylene, a latex compound or a vinyl acrylic, and an environmentally friendly antifouling biocidal composition comprising a grapefruit seed extract, a pomegranate extract, a *capsicum* preparation and a menthol, and optionally an additive in the form of one or more biocidal phytochemical agents.

7. The composition of Paragraph 6 wherein the coating composition is a marine coating suitable for application to a submerged surface or the submerged portion of an aquaculture system.

8. The composition of Paragraph 7 wherein the marine coating further comprises a rubber, silicone or acrylic adhesive.

9. The composition of Paragraph 6 wherein the optional one or more biocidal phytochemical agents is a camphor, a camphor oil, zosteric acid, *Zostera noltil*, partheniol, a lemon grass oil, a tea tree oil, a tannic acid, a tannin, a clove oil or a garlic.

10. The composition of Paragraph 1 or 6 wherein the composition further comprises at least one additive selected from the group consisting of a leaching paint, a ablative paints or a self-polishing coating, wherein the components of the additive comprise one or more of a primer, a resin, a pigment, a solvent, a paint binder and an anti-settling agent.

11. The composition of Paragraph 1 or 6 further comprising a chemical releaser that facilitates a controlled release of a biocidal phytochemical from the polymer.

12. The composition of Paragraph 11 wherein the chemical releaser is citric acid, zinc oxide, iron oxide, or vitamin E.

13. The composition of Paragraph 1 or 6 further comprising one or more additives selected from the group consisting of a wetting or emulsifying agent, a pH buffering agent, a gelling or viscosity enhancing agent, a preservative and a coloring agent.

14. The composition of Paragraph 1 wherein the *capsicum* preparation is about 1 ppm to about 2,000,000 ppm.

15. The composition of Paragraph 1 wherein the menthol is mentholpropyleneglycolcarbonate or a synthetic derivative thereof.

16. The composition of Paragraph 4 further comprising an extract from *Renilla reniformis*, wherein the extract comprises a diterpene, Renillafoulin A, Renillafoulin B, Renillafoulin C or any combination thereof.

17. A method of inhibiting the fouling of a submerged surface or the submerged portion of an aquaculture system comprising applying to a submerged or submersible surface or aquaculture system an antifouling coating comprising a composition according to Paragraphs 1 or 6.

18. The method of Paragraph 17, wherein the antifouling coating is attached to the submerged or submersible surface or aquaculture system by an adhesive.

19. An antifouling composition for inhibiting the growth of organisms on a surface, the composition comprising a menthol, a capsaicin-containing agent and tea tree oil.

20. An antifouling composition for inhibiting the growth of organisms a surface, the composition further comprising pomegranate extract, grapefruit seed extract, and at least one protease.

21. An antifouling composition for inhibiting the growth of organisms a surface, the composition comprising:
   a polymer base; and
   at least one antifouling composition according to paragraphs 19 or 20.

22. A method for treating a surface to discourage the colonization of the surfaces by organisms comprising the steps of:
   obtaining a composition according to paragraph 21;
   coating the surface of an object with the composition or structurally forming an object from the composition such that a surface of the object exposed to an aqueous environment is protected from colonization by an organism.

23. A method for treating a volume of water to discourage the proliferation of organisms therein comprising the steps of:
   obtaining a composition according to paragraphs 19 or 20;
   mixing the composition with water, thereby inhibiting the proliferation of organisms therein.

24. An antifouling coating comprising a composition according to paragraph 21.

25. A composition for inhibiting the growth of organisms in close proximity to a surface, the composition comprising:
   a base selected from the group consisting of an oil based paint, a water based paint, an acrylic paint, a marine paint and an architectural paint, an organic polymer, an inorganic polymer, a latex or a combination thereof, and at least one microencapsulated biocidal phytochemical agent dispersed within the base, said phytochemical being present in the base in an amount sufficient to inhibit the growth of bioorganisms that come in contact with a surface coated in the paint composition.

26. A composition according to paragraph 25 wherein the base is a paint, a wood treatment, a polymer coating or a structural polymer.

27. A method for treating surfaces to discourage the colonization of the surfaces by organisms comprising the steps of:

obtaining a composition comprising about 10% to about 99.5% by weight of a selected base material and at least one microencapsulated biocidal phytochemical component;

coating the surface of an object with the composition or structurally forming an object from the composition such that a surface of the object that may be colonized by an organism is protected from the colonization.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for inhibiting the colonization of a surface of an object by an organism, the method comprising:

coating the surface with a coating composition, said coating composition comprising: a base material selected from the group consisting of an hydrocarbon-based paint, a water-based paint, an acrylic paint, a marine paint and an architectural paint, an organic polymer, an inorganic polymer, and a latex, or a combination thereof; and a population of microcapsules dispersed within the base material, wherein the microcapsules are resistant to disruption by the base material and encapsulate a phytochemical-based composition, said phytochemical-based composition comprising menthol, a grapefruit seed extract, pomegranate seed extract, and a capsicum having capsaicin therein, wherein the phytochemical composition is present in the base material in an amount sufficient to inhibit the colonization of a bioorganism on the coated surface of the object.

2. The method of claim 1, wherein the phytochemical composition further comprises tea tree oil.

* * * * *